United States Patent [19]

Beuchat et al.

[11] Patent Number: 5,499,969
[45] Date of Patent: Mar. 19, 1996

[54] MICROSURGICAL CASSETTE

[75] Inventors: Charles E. Beuchat, Irvine; Roger Etherington, Newport Beach; Harold J. Walbrink, Laguna Niguel, all of Calif.; John W. Berkman, Grants Pass, Oreg.

[73] Assignee: Nestle S.A., Vevey, Switzerland

[21] Appl. No.: 274,935

[22] Filed: Jul. 14, 1994

Related U.S. Application Data

[62] Division of Ser. No. 135,865, Oct. 13, 1993, Pat. No. 5,364,342, which is a continuation of Ser. No. 831,766, Feb. 5, 1992, abandoned.

[51] Int. Cl.$^6$ .................................................. A61M 1/00
[52] U.S. Cl. ....................... 604/30; 604/151; 128/DIG. 12
[58] Field of Search .................................. 604/27, 30, 31, 604/35, 65, 118, 119, 151, 153; 128/DIG. 12, DIG. 13

[56] References Cited

U.S. PATENT DOCUMENTS

| | | |
|---|---|---|
| D. 264,134 | 4/1982 | Xanthopoulos . |
| 4,140,118 | 2/1979 | Jassawalla . |
| 4,187,057 | 2/1980 | Xanthopoulos . |
| 4,223,813 | 9/1980 | Garrett et al. . |
| 4,395,258 | 7/1983 | Wang et al. . |
| 4,398,542 | 8/1983 | Cunningham et al. . |
| 4,444,548 | 4/1984 | Andersen et al. . |
| 4,475,904 | 10/1984 | Wang . |
| 4,479,761 | 10/1984 | Bilstad et al. . |
| 4,493,695 | 1/1985 | Cook . |
| 4,526,515 | 7/1985 | DeVries . |
| 4,537,561 | 8/1985 | Xanthopoulos . |
| 4,626,248 | 12/1986 | Scheller . |
| 4,627,833 | 12/1986 | Cook . |
| 4,713,051 | 12/1987 | Steppe et al. . |
| 4,735,610 | 4/1988 | Akkas et al. . |
| 4,758,238 | 7/1988 | Sundblom et al. . |
| 4,773,897 | 9/1988 | Scheller et al. . |
| 4,790,816 | 12/1988 | Sundblom et al. . |
| 4,798,580 | 1/1989 | DeMeo et al. . |
| 4,838,865 | 6/1989 | Flank et al. . |
| 4,935,005 | 6/1990 | Haines . |
| 4,963,131 | 10/1990 | Wortrich . |
| 5,041,096 | 8/1991 | Beuchat et al. . |
| 5,106,366 | 4/1992 | Steppe . |
| 5,125,891 | 6/1992 | Hossain et al. . |
| 5,163,900 | 11/1992 | Wortrich . |
| 5,195,960 | 3/1993 | Hossain et al. . |

FOREIGN PATENT DOCUMENTS

| | | |
|---|---|---|
| 0319273 | 11/1988 | European Pat. Off. . |
| 2176717 | 1/1987 | United Kingdom . |

*Primary Examiner*—C. Fred Rosenbaum
*Assistant Examiner*—Frank Wilkens, III
*Attorney, Agent, or Firm*—Jeffrey S. Schira

[57] ABSTRACT

A cassette for use in combination with a surgical handpiece and a control console for controlling irrigation and/or aspiration fluid flows in the handpiece having a housing with an external surface and an interface adapted to be held in operative association with the control console, an inlet coupling, a pump tube having an inlet and a discharge line in fluid communication with a waste container and a fluid flow passage in fluid communication with the inlet coupling and the pump inlet consisting of an open channel formed in the external surface and a gasket adhered to the external surface to seal the channel fluid-tight.

25 Claims, 17 Drawing Sheets

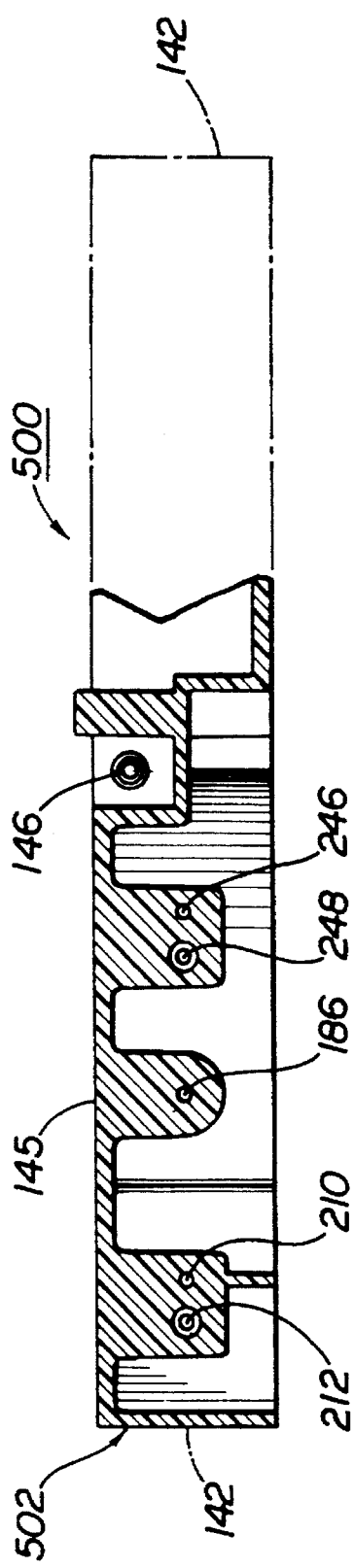
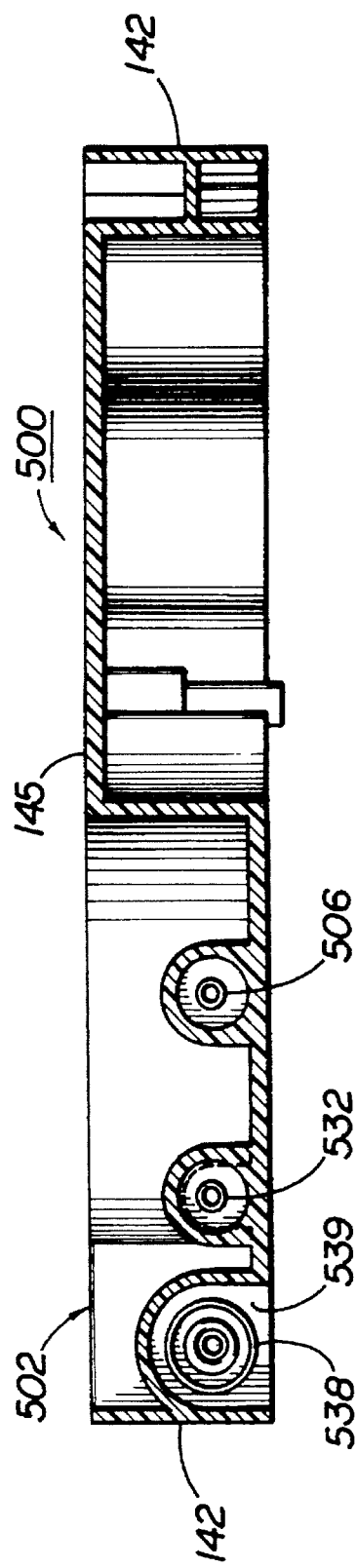
FIG. 15
FIG. 16

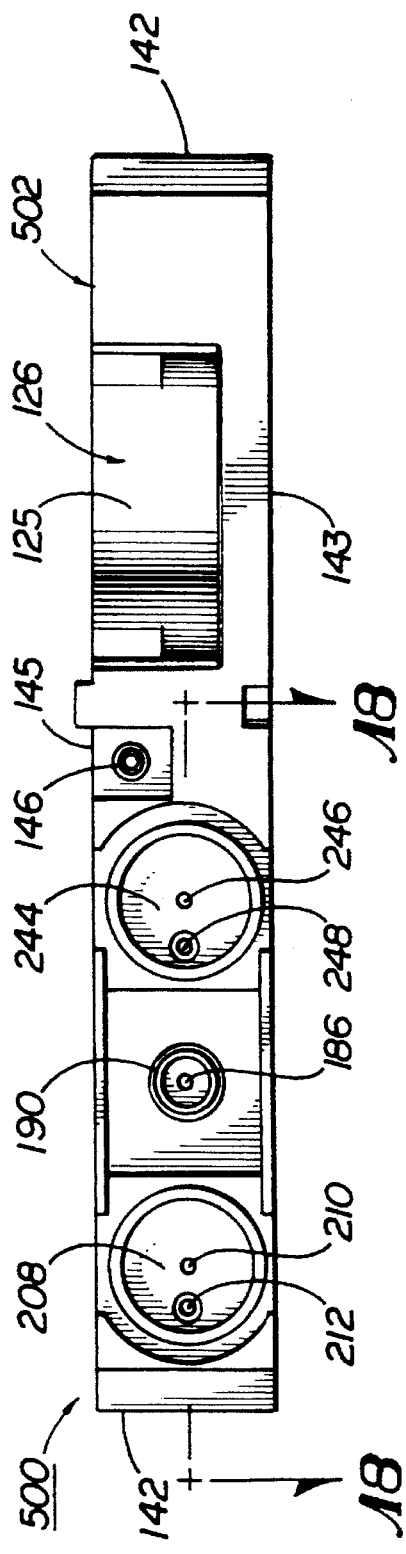
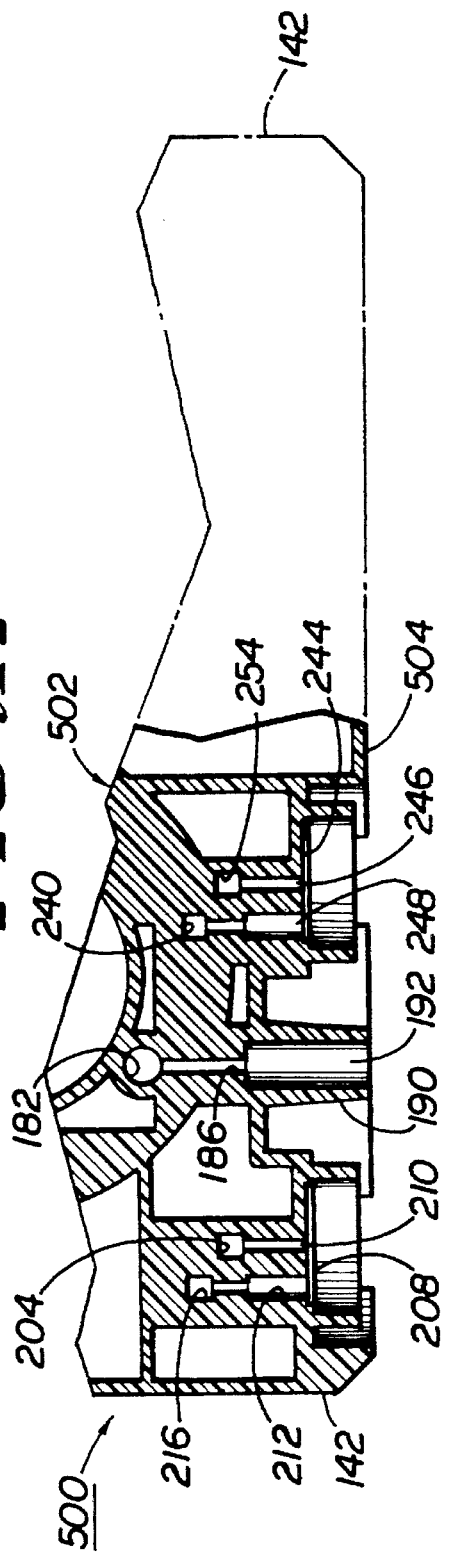
FIG. 17
FIG. 18

MICROSURGICAL CASSETTE

This is a division of application Ser. No. 08/135,865, filed on Oct. 13, 1993, currently U.S. Pat. No. 5,364,342, which was a File Wrapper Continuation of U.S. patent application Ser. No. 07/831,766, filed Feb. 5, 1992, now abandoned.

BACKGROUND OF THE INVENTION

Microsurgical instruments typically are used by surgeons for removal of tissue from delicate and restricted spaces in the human body, particularly in surgery on the eye, and more particularly in procedures for removal of the crystallin lens or the vitreous body. Such instruments include a control console and a surgical handpiece with which the surgeon dissects and removes the tissue. The handpiece has a surgical tool such as an ultrasonic microsurgical cutter for cutting or fragmenting the tissue and is connected to the control console by a long power cable and by long conduits or flexible tubes for supplying an irrigation fluid to the surgical site and for withdrawing or aspirating fluid and fragmented tissue from the site. The cutting, irrigation and aspiration functions of the handpiece are controlled by the remote control console that not only provides power for the surgical cutter (e.g., an ultrasonically vibrated needle), but also controls the flow of irrigation fluid and a provides a source of reduced pressure (relative to atmosphere) for the aspiration of fluid and fragmented tissue. The functions of the console are controlled manually by the surgeon, usually by means of a foot-operated switch.

The multiple connections that are required between the handpiece and the console for the power cable and the suction and irrigation lines have made the preparation and interconnection of the equipment prior to the surgical procedure extremely complex, with the resultant concerns over maintaining the sterility of the equipment and assuring error-free connection. Accordingly, in typical microsurgical instruments, the fluid handling connections have come to be centralized in a "cassette" that contains in one unit all of the connections for the aspiration and irrigation lines, Internal conduits for directing the flow of fluids, valves for controlling the flow of fluids into and out of the handpiece, a receptacle for aspirated fluid and tissue and may contain the tube portion of a peristaltic pump. The cassette typically is supplied in a sterile package with color-coded connecting tubing already attached. Thus, setting up the equipment requires only connecting the cassette tubing to the surgical handpiece and irrigation fluid source and inserting the cassette into a receptacle in the console. The receptacle may contain the roller head portion of a peristaltic pump (or some other access to reduced pressure), an aspiration line pressure sensor and devices for operating the valves in the cassette and for controlling the flow of irrigation or aspiration fluids through the fluid conduits within the cassette. For convenience and to maintain sterility, the cassette may be discarded after a single use or sterilized and reused.

Such a cassette is disclosed, for example in Steppe, et al., U.S. Pat. No. 4,713,051. The Steppe, et al., cassette is intended to cooperate with a control console that has the roller head element of a peristaltic pump as well as protruding occluder bars that can pinch or block the internal flexible tube conduits that carry fluids through the cassette. The cassette also has an irrigation transfer tube that vents irrigation fluid into the aspiration conduit to relieve quickly the reduced pressure created within the aspiration conduit of the cassette when the aspiration function is discontinued by the surgeon. When the cassette is installed in the console, an arcuate cutout on the top of the cassette containing the compressible tube portion of the peristaltic pump engages the roller head to supply a source of reduced pressure for the handpiece. The output of the peristaltic pump is collected in a flexible bag suspended from the cassette.

While the Steppe, et el., cassette has proved useful, the use of flexible tubes as internal fluid conduits requires accurate assembly of the tubes within the two-part housing of the cassette for proper operation, a complex, multi-step manufacturing process. Furthermore, the method of occluding fluid flow by pinching the flexible tubes relies entirely on the resilient properties and the quality of the tubes, variables that are not easily controlled during manufacture to assure consistent, predictable performance.

Another microsurgical cassette is disclosed in Sundblom, et el., U.S. Pat. No. 4,758,238. The Sundblom, et el., cassette uses channels molded into the body of the cassette and sealed by a stretchable covering gasket held taut against the molded body by a cover plate as internal fluid conduits. At certain points along the conduits, enlarged round chambers are formed in the conduits that allow enough room for the conduit to be blocked by valve stems stretching the gasket tightly against the conduit inlet to seal the conduit.

The Sundblom, et el., cassette requires not only the use of mechanical valves stems, but also that the gasket perform the dual function of serving as one wall of an extensive system of fluid conduits within the cassette and as a stretchable diaphragm to block the fluid flow at the selected locations. This dual function requires expensive gasket materials (i.e. silicone rubber), a multi-piece cassette and demanding assembly procedures, DeMeo, et el., U.S. Pat. No. 4,798,580, discloses a microsurgical cassette having a peristaltic pump tube within the cassette that cooperates with a roller drive on the console to provide a source of reduced pressure for the aspiration function of the microsurgical handpiece. The DeMeo, et al., cassette has a vent for venting the suction conduit to the atmosphere when the peristaltic pump is stopped. This vent consists of a flexible tube that is compressed and thereby pinched shut by an occluder bar in the console. The occluder bar pinches the tube, thereby closing the vent, whenever the peristaltic pump is operating and the bar is pulled away from the tube, thereby opening the vent, when the peristaltic pump is stopped to vent atmospheric air into the suction line. The DeMeo, et el., cassette has an irrigation fluid conduit consisting of an inlet port for connection to a source of irrigation fluid, an outlet port for connection to the tubing supplying irrigation fluid to the microsurgical handpiece and a flexible tube within the cassette connecting the inlet port and the outlet port. A portion of the tube can be alternatively pinched shut or opened to prevent or permit the flow of irrigation fluid by pressure from an occluder bar similar to the vent line occluder bar. The DeMeo, et el., cassette, by using compressible tubing as the control valves for the vent and irrigation fluid conduits and a two-part housing, has the same limitations as the Steppe, et el. cassette discussed above.

Accordingly, a need has continued to exist for a surgical cassette that is capable of simple and easy assembly while allowing the selection of reliable, predictable materials and structures for each function performed by the cassette at the lowest possible cost.

BRIEF SUMMARY OF THE INVENTION

The present invention is intended to improve upon prior art surgical cassettes by providing a cassette having a one-piece housing adapted to be held in operative association with a control console. Integrally formed channels on the external surface of the housing form three sides of various fluid flow passages within the cassette. A plastic gasket adhered to the (asserie seals the channels and forms the fourth side of the fluid flow passages. A pump may be self-contained within the cassette and adapted to cooperate with a source of motive power contained in the console.

The structure of the present invention may be modified or additional elements or structures added to adapt the cassette for use with different consoles. For example, in a first embodiment, a portion of an interface is cut away and a pump race having an arcuate indentation holds the resilient tube of a peristaltic pump. The tube is connected to an aspiration fluid flow passage and the lower portion of the tube forms a discharge line that exits the cassette. An interface area on the console contains the roller head assembly of a peristaltic pump that is inserted into the interface wall cutout and against the indentation when the cassette is installed in the console, thereby compressing and holding the tube tightly between the roller head and the pump race indentation. The discharge line is connected to a waste container suspended from the cassette.

In a second embodiment of the present invention, the housing contains an integral waste container in fluid communication with the discharge line.

In contrast to the first and second embodiments, a third embodiment of the present invention contains an integrally formed waste container spaced in the aspiration fluid flow passage between the aspiration fluid inlet and the pump and an aspiration fluid valve is inserted into the aspiration fluid flow passage between the aspiration fluid inlet and the waste container.

A fourth embodiment of the present invention contains all of the elements of the first embodiment and further includes an irrigation fluid inlet and outlet and an irrigation fluid flow passage having an irrigation fluid valve and connecting the irrigation fluid inlet to the irrigation fluid outlet. The irrigation fluid outlet is connected to the surgical handpiece by flexible tubing and the peristaltic pump discharge line is connected to a waste container suspended from the cassette.

A fifth embodiment of the present invention contains all the elements of the fourth embodiment and further includes a vent conduit in the aspiration fluid flow passage between the aspiration fluid inlet and the pump tube that connects to a vent valve contained within the console.

A sixth embodiment of the present invention contains all the elements of the fifth embodiment except the vent valve is contained within the vent conduit and the vent conduit connects the aspiration fluid flow passage to the irrigation fluid flow passage.

A seventh embodiment of the present invention contains all the elements of the sixth embodiment and further includes a pressure sensor contained within the aspiration fluid flow passage between the aspiration fluid inlet and the vent conduit that cooperates with a pressure sensor in the interface area on the console.

The present invention eliminates the need to use flexible tubing as the internal fluid conduits within the cassette, thereby simplifying the assembly of the cassette and reducing manufacturing costs.

Accordingly, one objective of the present invention is to provide, in a single disposable unit, a surgical cassette containing all the necessary passages and connections for providing fluid flow between a control console and a surgical handpiece.

Another objective of the present invention is to provide a surgical cassette that is simple and inexpensive to manufacture.

Still another objective of the present invention is to provide a surgical cassette having a one-piece housing.

Another objective of the present invention is to provide a simple surgical cassette containing an integral waste container.

Another objective of the invention is to provide a surgical cassette having a simple and efficient valve for allowing the console to control the fluid to or from the handpiece.

Still another objective of the present invention is to provide a surgical cassette having valves that are simple to manufacture and operate, yet provide an effective, reliable occlusion of fluid flow.

Still another objective of the present invention is to provide a surgical cassette having valves that exhibit fast response and are operable by light load solenoids in the console.

A further objective of the present invention is to provide a surgical cassette having valves with improved reliability.

A further objective of the present invention is to provide a surgical cassette having a pressure sensor in a conduit connected to the handpiece.

Additional objects and advantages of the present invention will become apparent to those skilled in the art from the detailed description and drawings that follow.

BRIEF DESCRIPTION OF THE DRAWINGS

FIG. 15 is a partial cross sectional view of the cassette shown in FIG. 14 taken along line 15—15, FIG. 16 is a longitudinal cross sectional view of the cassette shown in FIG. 14 taken along line 16—16.

FIG. 17 is an elevational view of the interface wall of the cassette shown in FIG. 10.

FIG. 18 is a partial cross sectional view of the cassette shown in FIG. 17 taken along line 18—18.

DETAILED DESCRIPTION OF THE DRAWINGS

Figure 7:
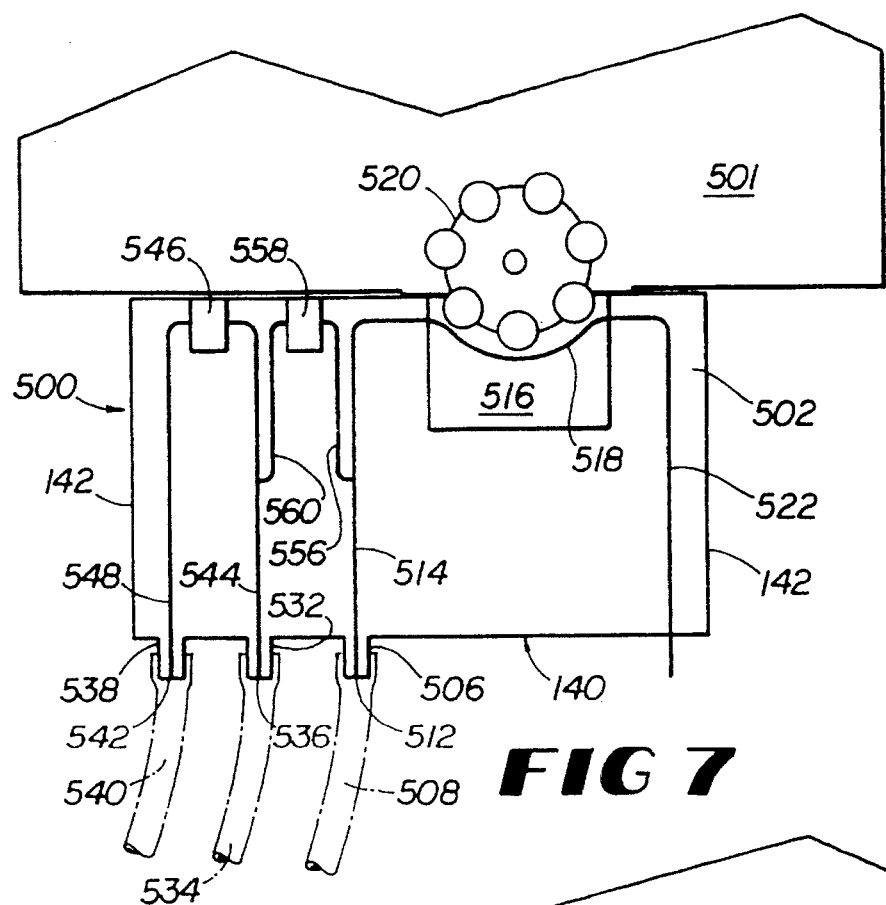
FIG. 7 is a schematic view of the sixth embodiment of the cassette of the present invention.
Figure 8:
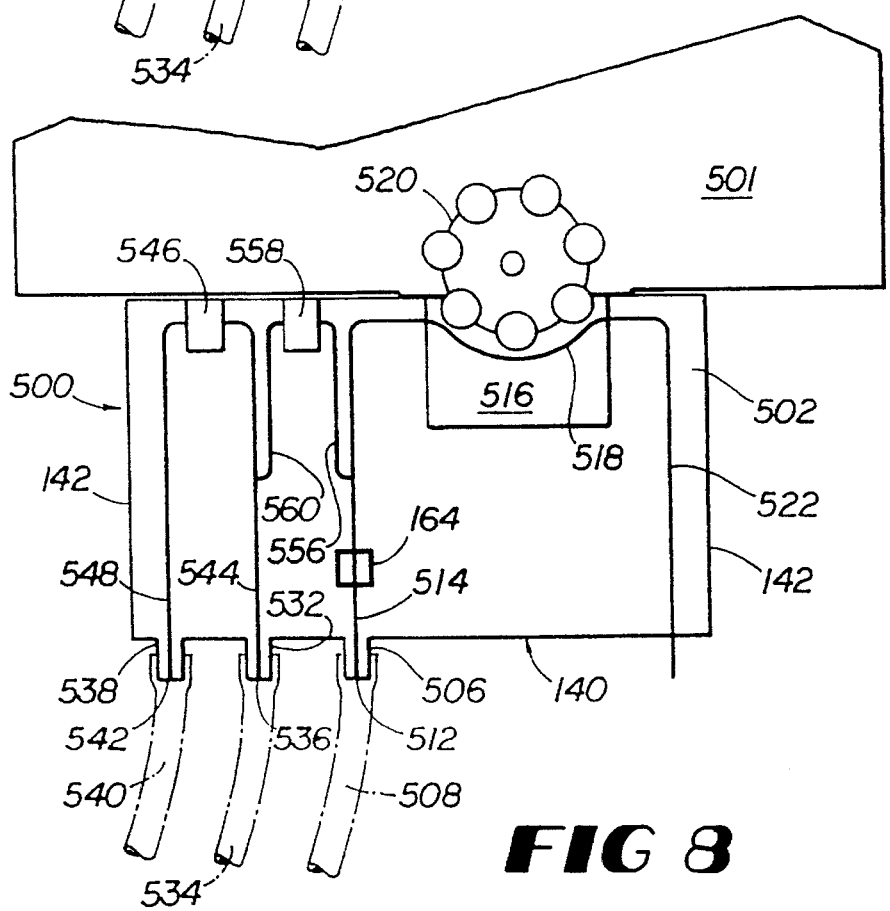
FIG. 8 is a schematic view of the seventh embodiment of the cassette of the present invention.
Figure 9:
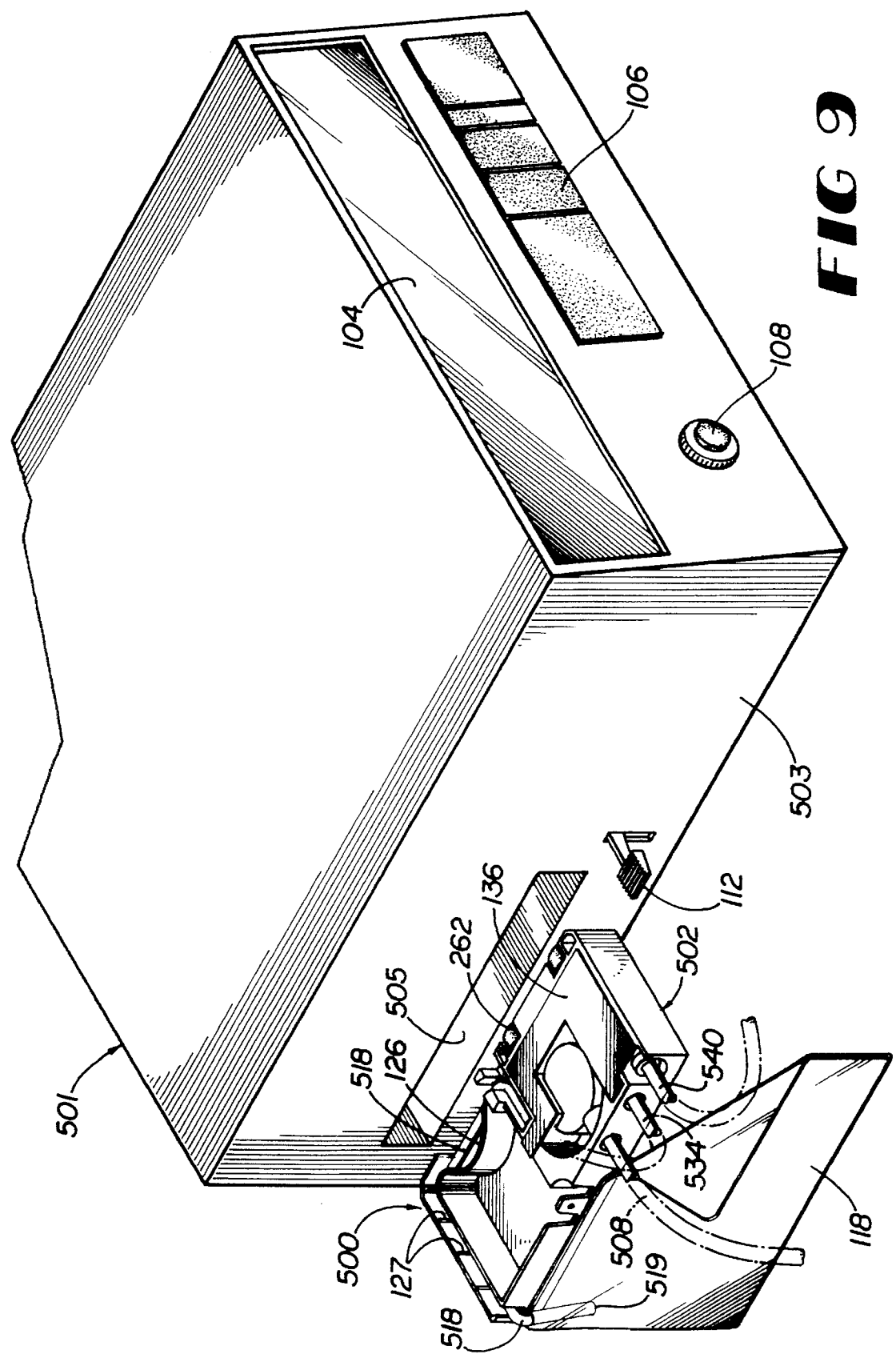
FIG. 9 is an exploded perspective view of a surgical instrument console using the cassette of the present invention.

As can be seen schematically in FIGS. 1 to 9 and 27, cassette 500 of the present invention generally comprises housing 502 having interface wall 504 that, when cassette 500 is in use, is held within slot 505 of console 501, a portion of which is indicated schematically in FIG. 9. Console 501 contains a means (not shown) for securing cassette 500 with interface wall 504 in operative association with interface slot 505 of console 501, a means (not shown) for actuating any valve or pump 516 in cassette 504 or, alternatively, a source of motive power (not shown) for operating pump 516 within cassette 504. Front wall 140, opposite interface wall 504 contains coupling 506 having aspiration fluid inlet port 512. Pump 516 communicates with aspiration fluid inlet port 512 through channel 514, which is integrally formed in housing 502 and contains discharge line 522, that also can be integrally formed in housing 502 or may be a resilient tube. Housing 502 is preferably made of injection-molded medical grade plastic but other suitable materials and manufacturing methods can also be used.

Coupling 506 may be any conventional type of coupling for making a fluid-tight junction between two fluid conduits. For example, coupling 506 may be a generally cylindrical fitting protruding from housing 502 and having a smooth or barbed exterior as preferred. Coupling 506 may be a tapered fitting such a male or female luer connector adapted to mate with a corresponding portion of the luer connector on housing 502. Coupling 506 may also be any conventional screw coupling, clamped coupling, quick-release hydraulic fitting or the like all of which are well-known. A preferred coupling 506 is a cylindrical or tapered friction fitting integrally molded in housing 502.

Pump 516 also may be a peristaltic pump, a diaphragm pump operated by a mechanical plunger (not shown) driven by a mechanism (not shown) in console 501. Diaphragm pump 516 may also be driven by an electric motor (not shown) or an electromagnetically driven plunger (not shown) such as a solenoid-operated plunger (not shown) located in cassette 500 and supplied with electric power from a source (not shown) located within console 501. Alternatively, pump 516 may be a reciprocating piston pump, a rotary vane pump, a centrifugal pump, venturi pump or any other pump capable of withdrawing fluid from fluid conduit 514 and expelling the fluid through discharge line 522. However, self-priming pumps are preferred. The flow rate and the corresponding pressure level in conduit 514 may be varied by adjusting the speed of pump 516.

Figure 1:
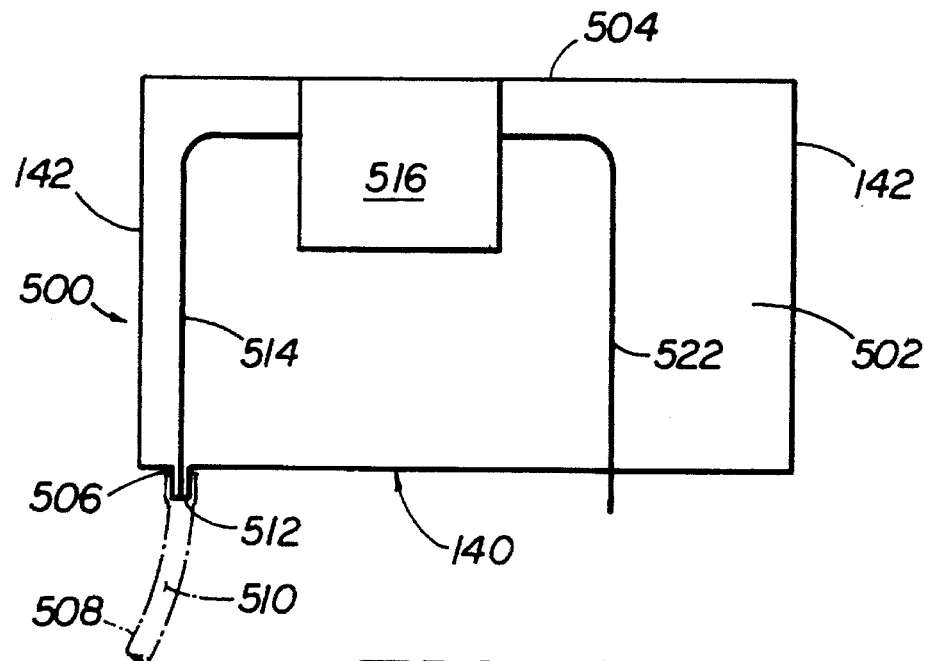
FIG. 1, is a schematic view of the cassette of the present invention.
Figure 2:
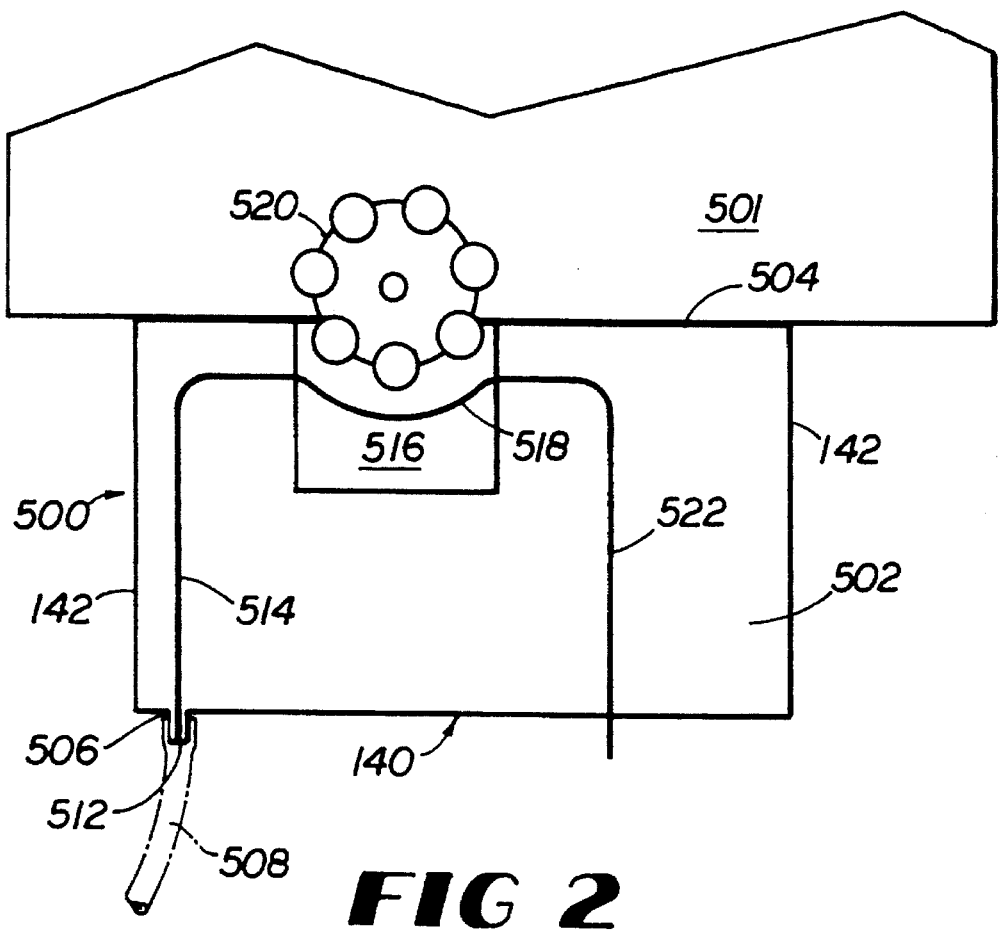
FIG. 2 is a schematic view of the first embodiment of the cassette of the present invention.
Figure 10:
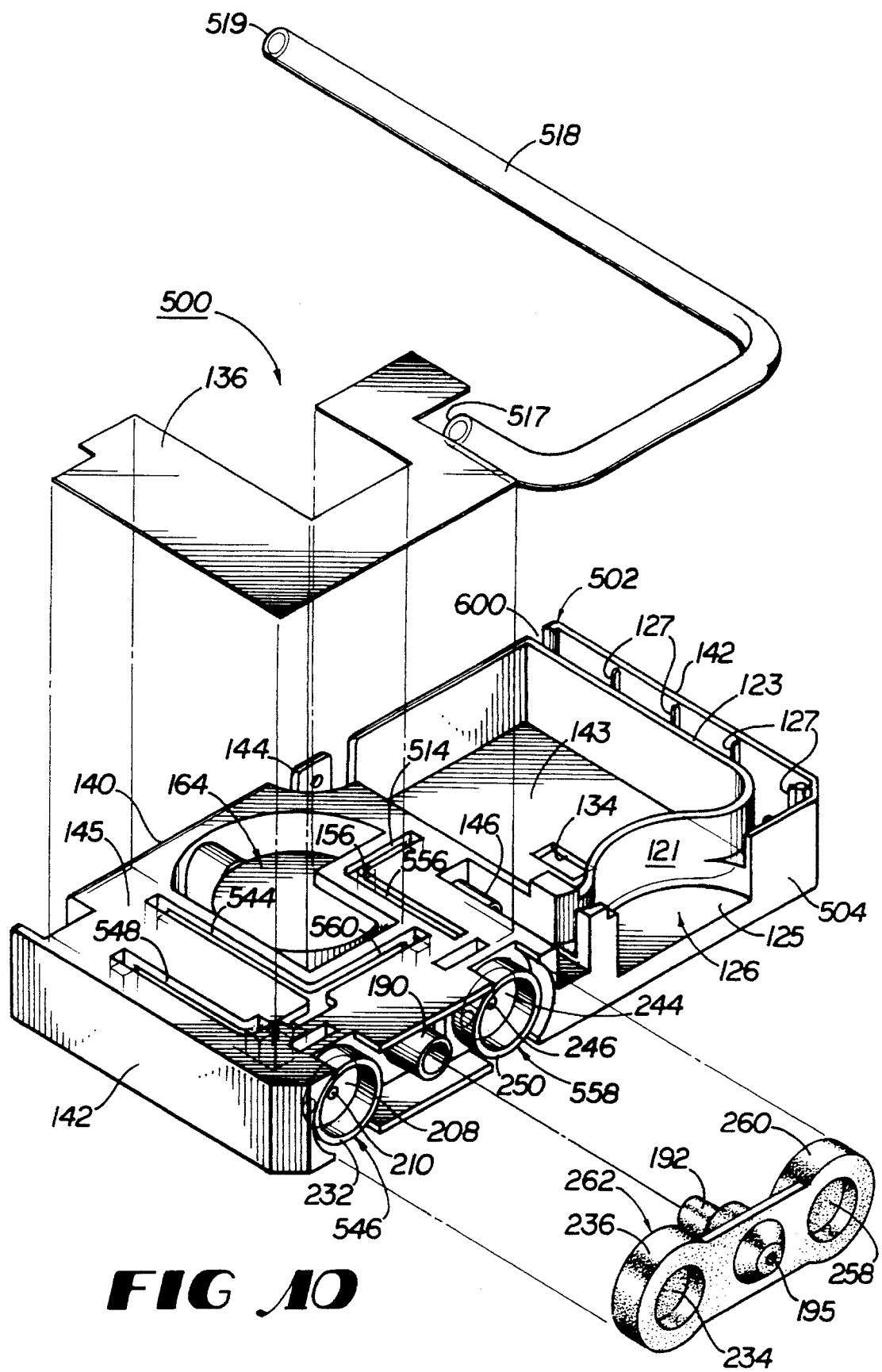
FIG. 10 is an exploded assembly drawing of the seventh embodiment of the cassette diagrammed schematically in FIG. 8.

In a first embodiment of the present invention, illustrated schematically in FIG. 2, cassette 500 contains pump tube 518 that is held within housing 502 and is connected on one end to aspiration fluid inlet port 512 in coupling 506 through internal conduit 514. Coupling 506 is connected to aspiration line 508 of surgical handpiece 10. Tube 518 is connected at the end opposite internal conduit 514 to discharge line 522 or, alternatively, the length of tube 518 may be extended to form discharge line 522. Discharge line 522 empties into waste container 118 that may be a flexible plastic bag suspended from the cassette as shown in FIG. 9 or another external container (not shown). Conduit 514 is preferably integrally molded into housing 502. In particular, conduit 514 may be molded as a channel in housing 502 and top gasket 136, as shown in FIG. 10, may be adhered over the channel to form sealed conduit 514.

Pump 516 is a peristaltic pump consisting of compressible tube 518 that cooperates with a roller head 520 mounted in interface slot 505 on console 501 and driven by a source of motive power (not shown) such as an electric motor (not shown) located within console 501. When interface wall 504 of housing 502 is installed in interface slot 505 of console 501, roller head 520 presses against tube 518. Rotation of roller head 520 forces aspiration fluid through tube 518 and out discharge line 522 by peristaltic action, resulting in an area of reduced pressure within tube 518 at the upstream or inlet port 512 side of roller head 520. The reduced pressure created by the rotation of roller head 520 against tube 518 draws aspiration fluid from aspiration line 508 into inlet port 512 and toward roller head 520 through internal conduit 514 where the aspiration fluid is forced out discharge line 522. The speed of roller head 520 can be varied by devices (not shown) that are well-known in the art.

Figure 3:
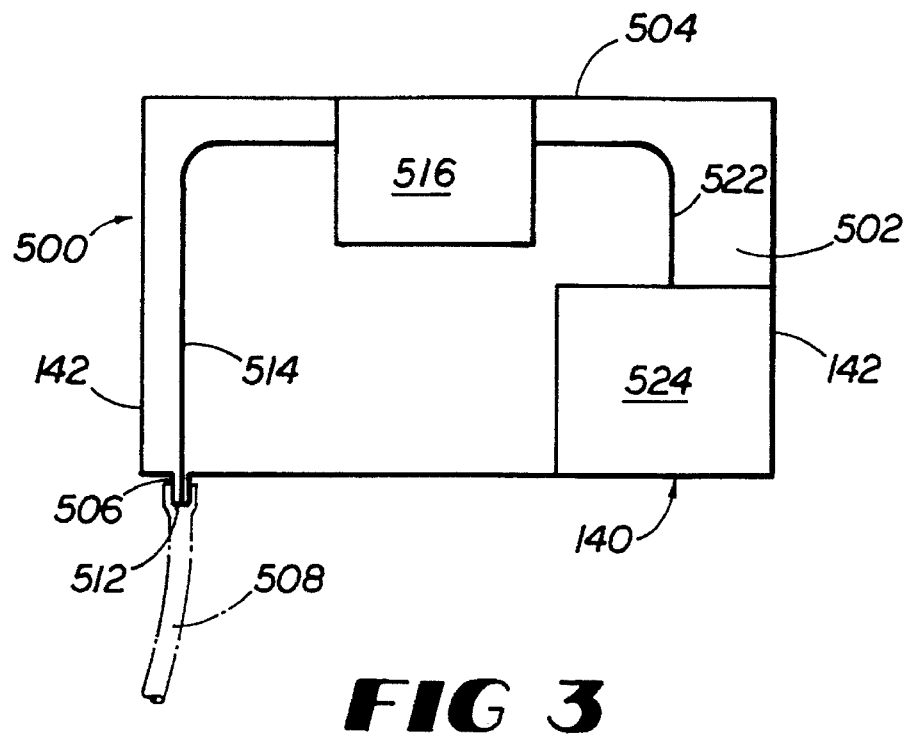
FIG. 3 is a schematic view of the second embodiment of the cassette of the present invention.

A second embodiment of the present invention, illustrated schematically in FIG. 3, is similar to the first embodiment, differing only in that discharge line 522 empties into waste receptacle 524 that is integrally molded into housing 502, rather than externally suspended bag 118.

Figure 4:
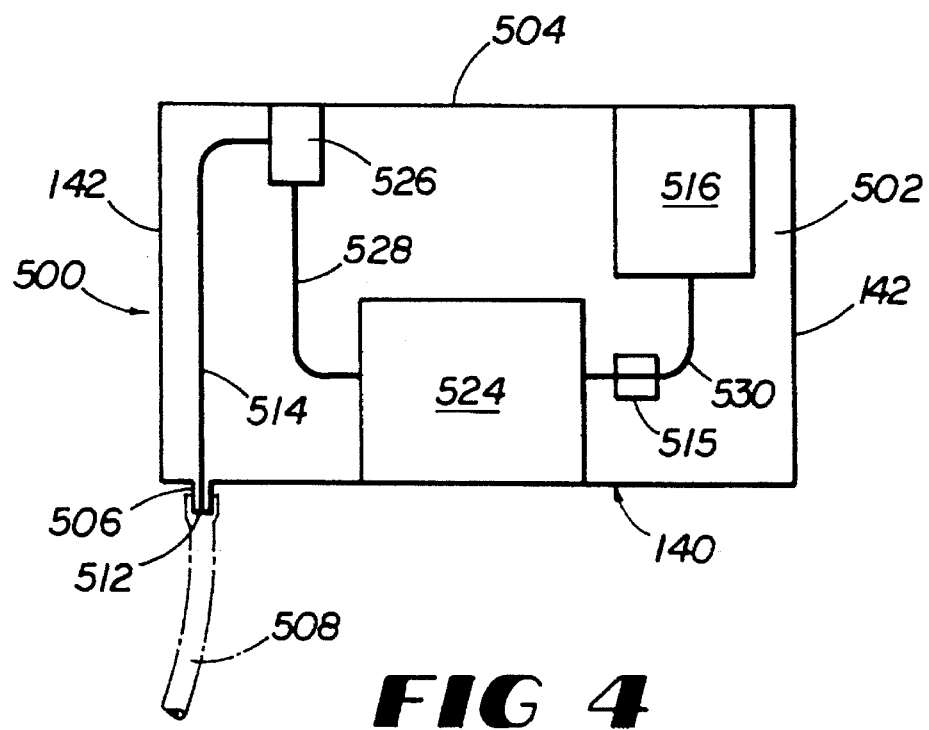
FIG. 4 is a schematic view of the third embodiment of the cassette of the present invention.

In a third embodiment of the present invention, illustrated schematically in FIG. 4, cassette 500 contains coupling 506, aspiration fluid inlet port 512, internal conduit 514, aspiration fluid flow control valve 526, aspiration fluid transfer conduit 528, integral waste receptacle 524, suction conduit 530 and pump 516. Pump 518 withdraws atmospheric air from waste container 524 through suction conduit 530, thereby reducing the pressure in waste container 524 and drawing aspiration fluid through aspiration line 508, inlet port 512, conduit 514, valve 526 and transfer conduit 528 and into waste container 524. In this embodiment, it is preferred that the aspirated fluid not reach pump 516 and filter 515, capable of permitting the passage of gas but excluding liquid, such as a hydrophobic or hydrophobic/hydrophilic filter, may be inserted in suction conduit 530. Pump 516 may be any type of vacuum pump capable of withdrawing air from waste container 524 and producing the reduced pressure needed for the operation of the aspiration function of surgical handpiece 10. For example, pump 516 may be a diaphragm pump or a venturi pump. Conduits 514, 528 and 530 are preferably integrally molded into housing 502. In particular, conduits 514, 528 and 530 may be molded as open channels in housing 502 and top gasket 136, as shown in FIG. 10, may be placed over the channels to form sealed conduits.

Figure 23:
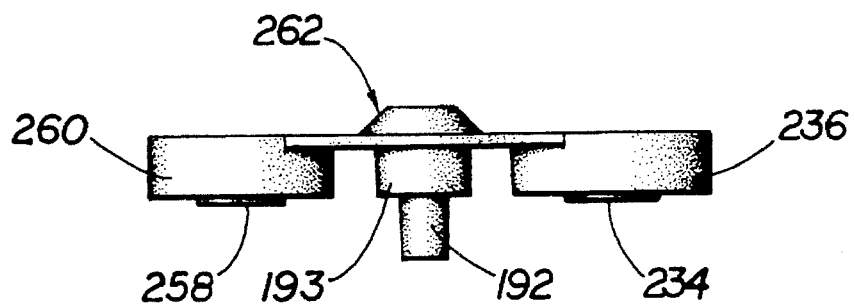
FIG. 23 is an elevational view of the molding containing the diaphragm valves and vacuum sensor sealing grommet.
Figure 24:
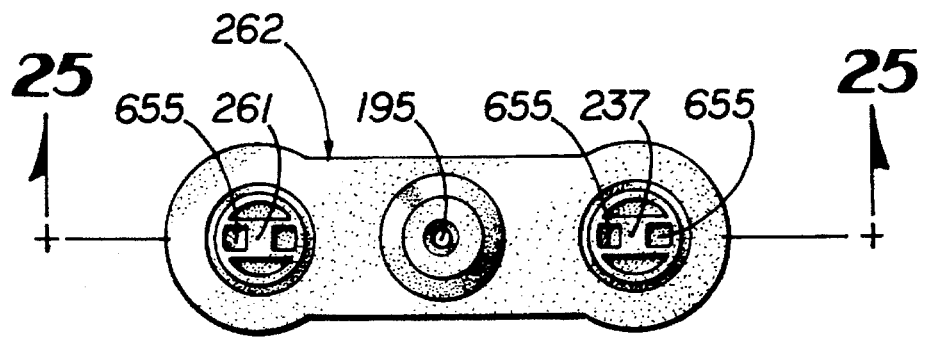
FIG. 24 is a top plan view of the molding containing the diaphragm valves and vacuum sensor sealing grommet shown in FIG. 23.
Figure 25:
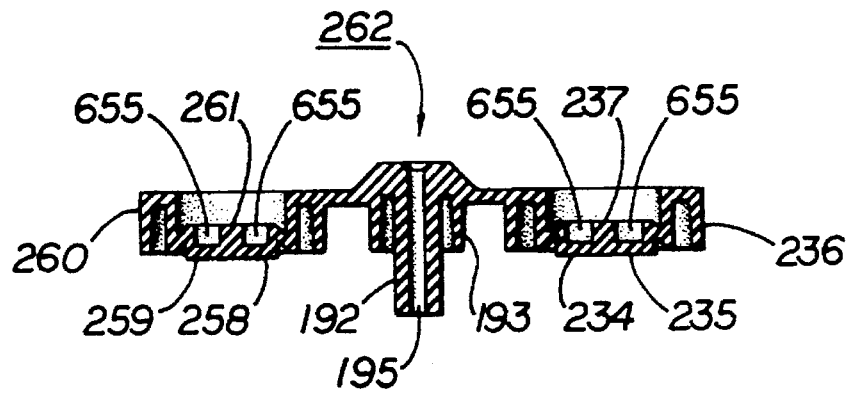
FIG. 25 is a cross section of the molding shown in FIG. 24 taken along line 25—25.

Valve 526 preferably is located proximate to interface wall 504 of cassette 500 so that it can be actuated by an actuation means (not shown) in console 501 and may be any type of valve that is capable of shutting off the flow of a fluid. Thus, a sliding gate valve, a ball valve, a stopcock or the like can be used. A preferred valve is a diaphragm valve, as illustrated in FIGS. 23, 24 and 25, wherein a movable sealing diaphragm (similar to diaphragms 234 or 258) may be moved between an open position wherein fluid is permitted to flow through orifices (not shown) within valve 526 and a closed position wherein the diaphragm (not shown) blocks the flow through at least one of the internal orifices (not shown) of valve 526. The structure and operation of preferred diaphragm valves is more fully described below in the description of the seventh embodiment of the present invention.

Figure 5:
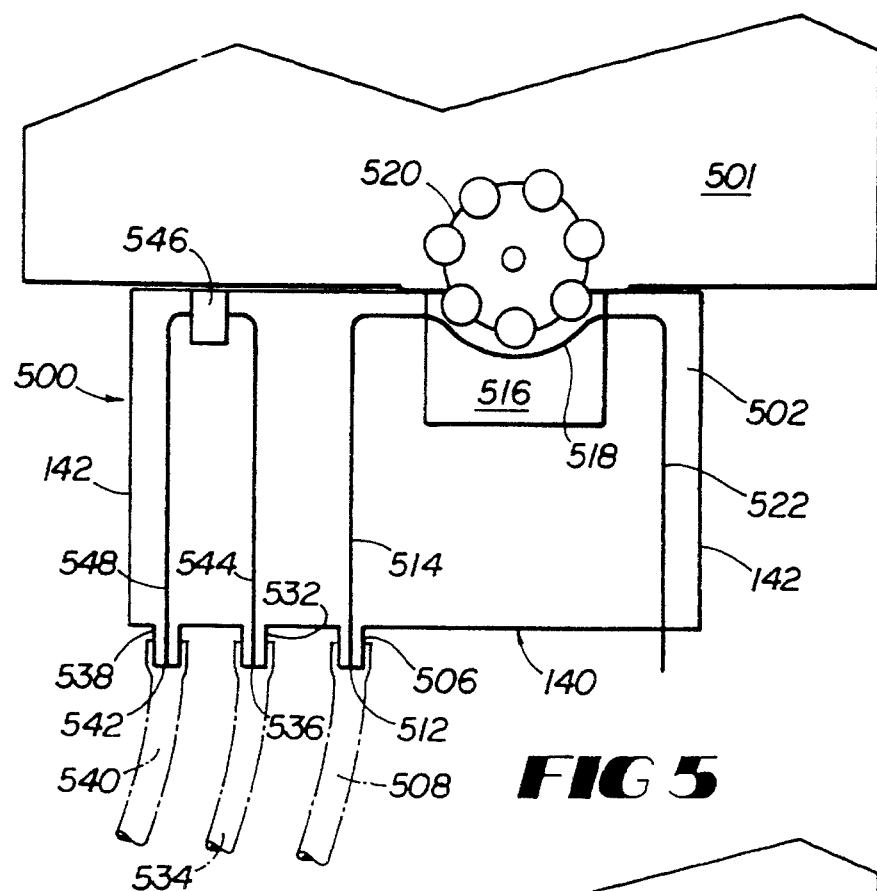
FIG. 5 is a schematic view of the fourth embodiment of the cassette of the present invention.

In a fourth embodiment of the present invention, illustrated schematically in FIG. 5, cassette 500 is similar to the second embodiment and contains all the elements of the second embodiment but further includes internal irrigation fluid conduits 544 and 548, an irrigation fluid valve 546 for controlling the flow of irrigation fluid to surgical handpiece 10, an irrigation fluid inlet coupling 532 having an inlet port 536 for connection to an irrigation fluid inlet tube 534 and an irrigation fluid outlet coupling 538 having an outlet port 542 for connection to an irrigation fluid outlet tube 540. Couplings 532 and 538 may be constructed essentially the same as coupling 506. Inlet port 536 communicates with irrigation fluid inlet conduit 544 which conducts the irrigation fluid to valve 546. Similarly, Irrigation fluid outlet conduit 548 conducts the irrigation fluid from valve 546 to outlet port 542. Valve 546 is similar to valve 526 and actuated in the same manner as valve 526 by a control means (not shown) located in console 501. Irrigation fluid conduits 544 and 548 are preferably integrally molded in housing 502 and constructed in the same manner as conduits 514, 528 and 530.

It will be understood that, although cassette 500 of FIG. 5 contains elements for performing both the irrigation and aspiration functions, it is not necessary that these elements be combined in a single cassette. Just as cassettes 500 in FIGS. 1–4 contain only elements for performing the aspiration function, it is possible to have cassette 500 according to the present invention that contains only the irrigation elements (couplings 532 and 538, ports 512 and 542, irrigation fluid tubes 534 and 540, conduits 44 and 548 and valve 546) of cassette 500 illustrated in FIG. 5.

Figure 6:
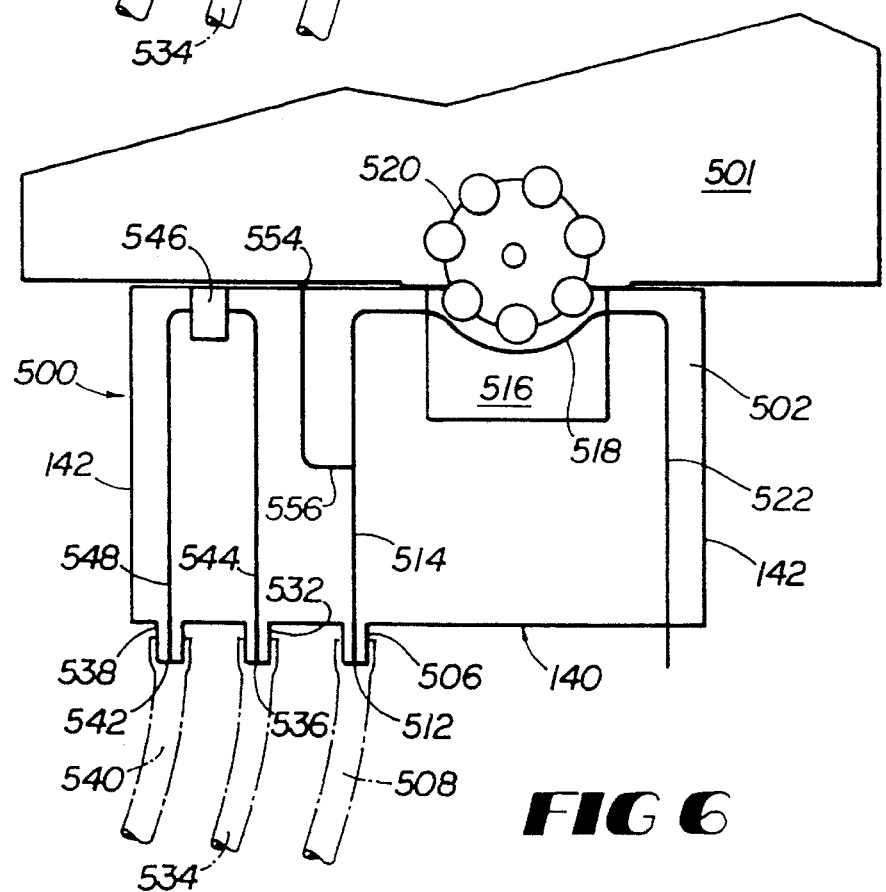
FIG. 6 is a schematic view of the fifth embodiment of the cassette of the present invention.

A fifth embodiment of the present invention, illustrated schematically in FIG. 6, cassette 500 is similar to cassette 500 of the fourth embodiment described above in that cassette 500 contains elements for controlling the flow of aspiration and irrigation fluid. However, cassette 500 further contains a vent line 556 that intersects aspiration fluid conduit 514 between aspiration fluid inlet port 512 and pump 516 at one end and terminates at a vent port 554 on interface wall 504. Vent port 554 communicates with a vent valve (not shown) located in console 501 and allows the surgeon to eliminate the reduced pressure within conduit 514 and stop the aspiration function as quickly as possible when the aspiration and cutting functions of handpiece 10 are suspended.

A sixth embodiment, illustrated schematically in FIG. 7, is similar to the fifth embodiment illustrated in FIG. 6 except cassette 500 does not contain vent port 554. Instead, vent line 556 terminates in a vent valve 558 located in cassette 500. Vent valve 558 is further in communication with irrigation conduit 544 through irrigation vent 560. This arrangement of vent line, vent valve and irrigation vent permits irrigation fluid rather than air to enter aspiration fluid conduit 514 when the surgeon interrupts the cutting function of handpiece 10. Vent valve 558 is actuated by a means (not shown) in console 501 in the same manner as irrigation valve 546. The preferred types of vent valve 558 are the same as for the irrigation valve 546 and aspiration control valve 526 described above.

A seventh embodiment of the present invention, illustrated schematically in FIG. 8 and more particularly in FIGS. 10–27, contains all the elements of the sixth embodiment described above and further includes a pressure indicating chamber 164 within aspiration conduit 514 that cooperates with a pressure sensor (not shown) in console 501 to indicate the pressure level within conduit 514 in a manner that will be described more fully below. Alternatively, chamber 164 may include devices, such as capacitor-forming electroplates (not shown), that sense the pressure and/or fluid flow within chamber 164 directly.

Figure 27:
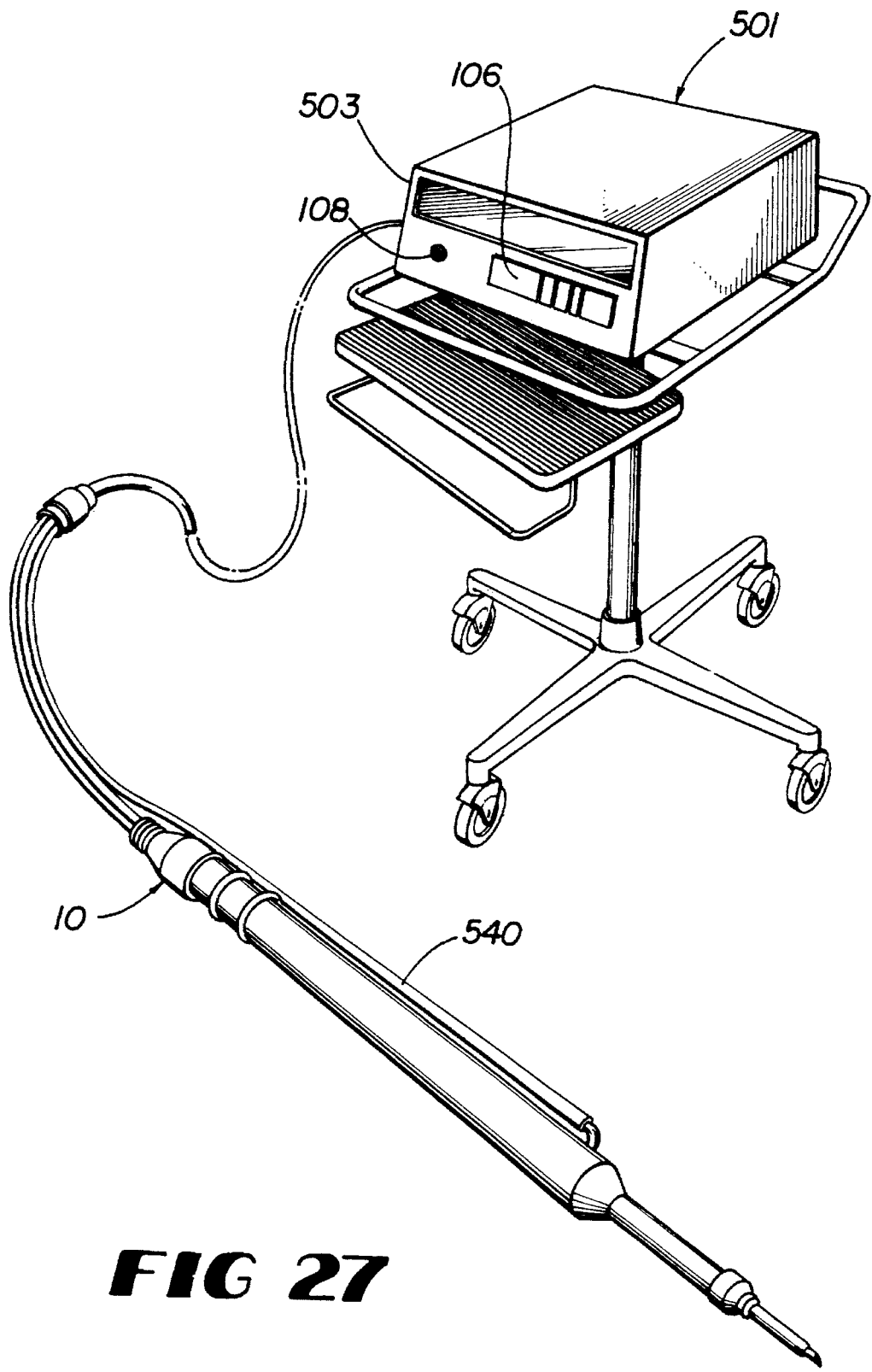
FIG. 27 is a perspective view of a surgical instrument.

As can be seen in FIGS. 9, 10, 11 and 12, cassette 500 of the seventh embodiment of the present invention generally comprises housing 502, waste container 118, top cover gasket 136, compressible tube 518, valve molding 262, elastic diaphragm 166, diaphragm cover 170 and bottom cover gasket 184. As can be seen in FIGS. 9 and 27, cassette 500 is used in combination with a surgical instrument having console 501 and handpiece 10 used by the surgeon to fragment tissue at a surgical site, supply irrigation fluid to the surgical site and aspirate the fragmented tissue and irrigation fluid from the site. Console 501 contains display panel 104 that displays the current control settings and operating parameters of the instrument. Control panel 106 on console 501 includes switches (not shown) to control the various conditions of operation of the instrument. Start button 108 initiates operation of the instrument. Side 503 of console 501 contains interface slot 505 that accepts cassette 500. Within interface slot 505 are mechanisms (not shown) for holding cassette 500 securely within interface slot 505 and actuating valves 546 and 558 and for operating peristaltic pump 516. These mechanisms (not shown) will vary from console to console according to the particular embodiment of cassette 500 which is used with a particular console 501, and these mechanisms do not form part of this invention.

Figure 11:
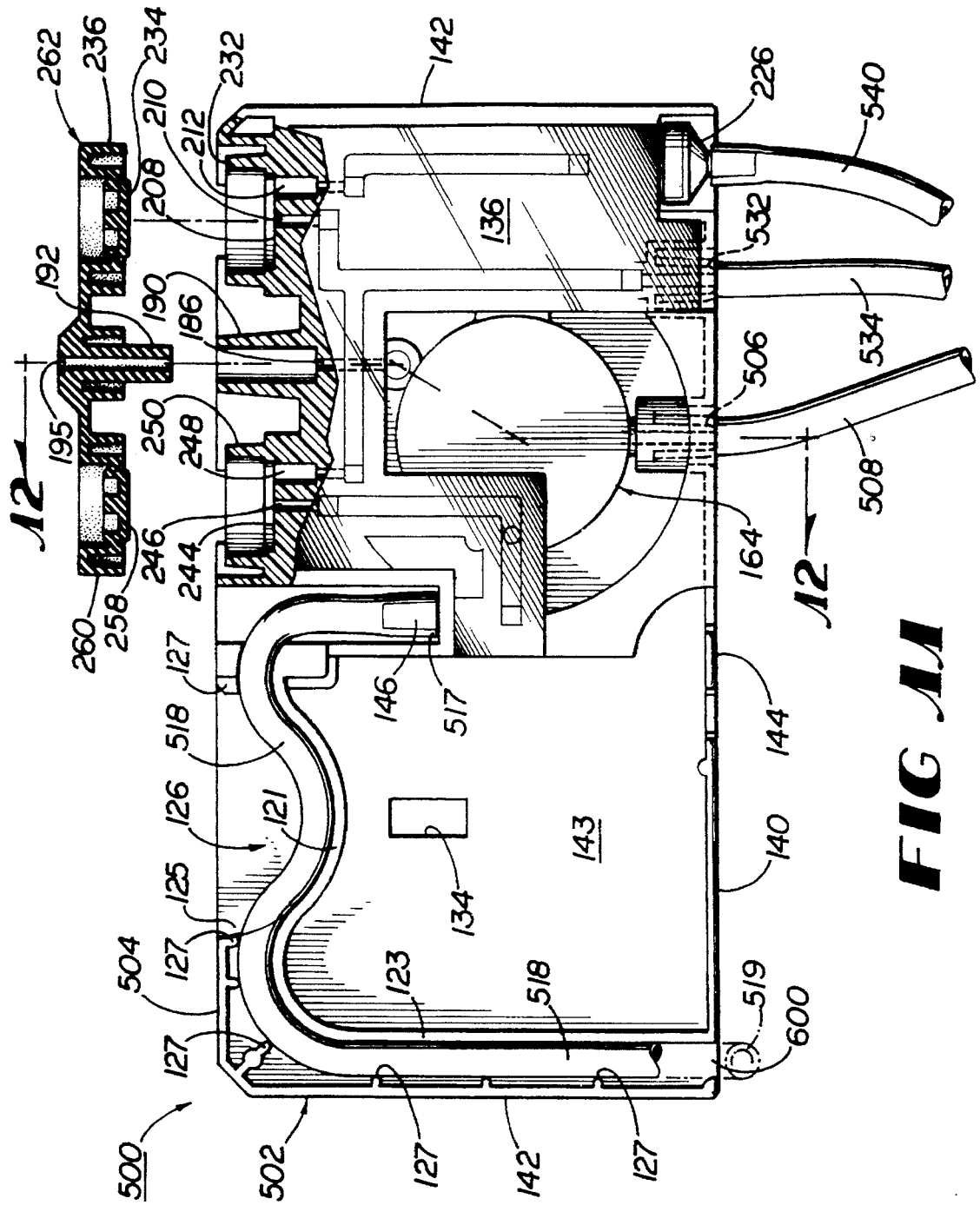
FIG. 11 is a top plan view of the cassette illustrated in FIG. 10, partially cut away, with a cross sectional view of the valve and pressure sensor sealing grommet molding exploded away from the cassette.

As can be seen in FIGS. 10, 11, 13 and 14, housing 502 consists interface wall 504, front wall 140 opposite interface wall 504, top 145, bottom 143, side walls 142 and is preferably constructed in one piece from injection molded medical grade thermoplastic. As can be seen in FIGS. 10 and 11, top 145 contains horizontal conduits 514, 544, 548, 556 and 560, coupling 146 and peristaltic pump race 126. Conduits 514, 544, 548, 556 and 560 are generally square channels integrally molded in top 145 of housing 502. Coupling 146 is integrally molded in housing 502 and is of similar construction as coupling 506. Pump race 126 is open at top 145 and is bordered on one side by wall 142 of housing 502 and on the other side by a generally J-shaped, thin wall 123 projecting upward from bottom 143 that is integrally molding in housing 502 and contains a semicircular depression 121 at the base of the J near interface wall 504. Pump race 126 accepts peristaltic tube 518 having an inlet end 517 that frictionally engages coupling 146 in top 145 that is in fluid communication with conduit 514 and a discharge end 519 that threads around pump race 126 and exits housing 502 at notch 600. Discharge end 519 of tube 518 may be connected to waste container 118 or to some other device (not shown). As can be seen in FIG. 11, tube 518 is held tight within race 126 by friction tabs 127 molded into race 126. In this embodiment, discharge line 522 is not necessary because tube 518 is of sufficient length to exit cassette 502 at notch 600.

Figure 12:
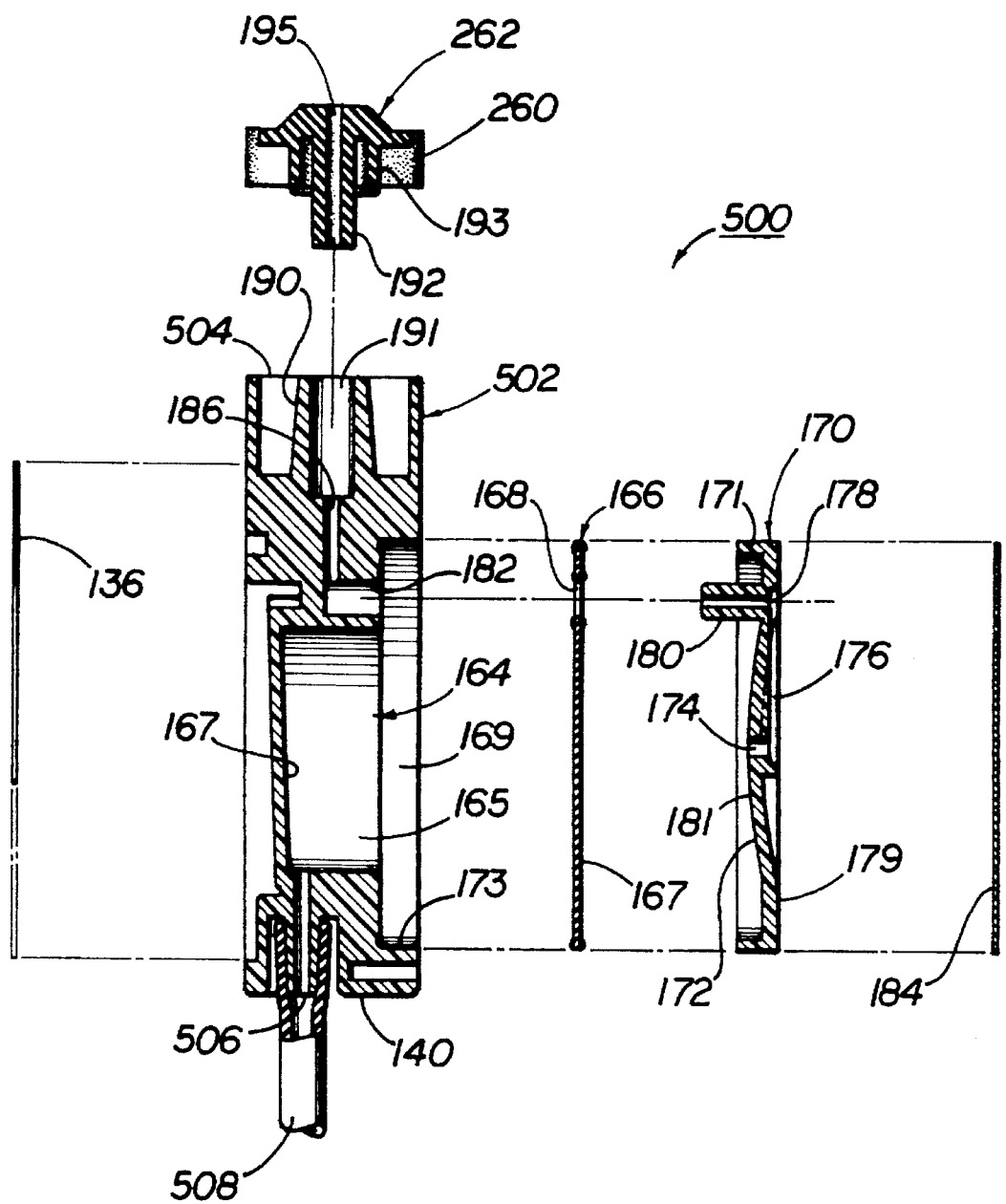
FIG. 12 is an exploded cross section of the cassette, valve and grommet molding of FIG. 11 taken along the line 12—12.
Figure 14:
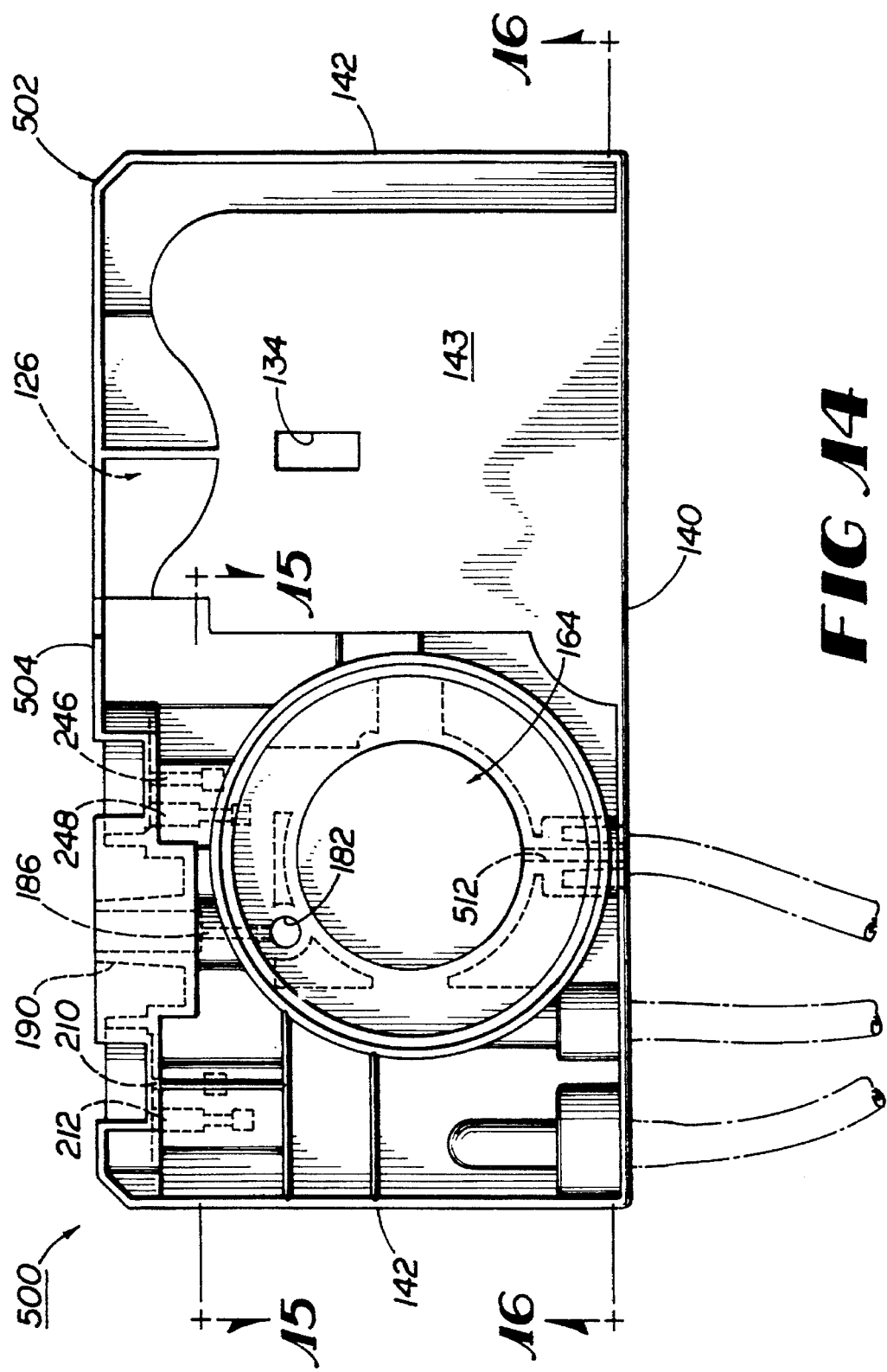
FIG. 14 is a bottom plan view of the cassette shown in FIG. 10 with the bottom gasket, diaphragm and diaphragm support removed.

Bottom 143 of housing 502 contains pressure sensing chamber 164 and solid portion 133 having cassette retaining slot 134. Retaining slot 134 cooperates with a cassette retaining arm (not shown) on console 501 to retain cassette 500 within interface area 505. The control arm (not shown) is operated by control lever 112 on side 503 of console 501. As can be seen in FIGS. 10, 12 and 14, pressure sensing chamber 164 is generally round and consists of a thin-walled vertical cylinder 165 having a closed, slanted end 167 near top 145 and an open, generally T-shaped end 169 having a recess 173 of slightly larger diameter than cylinder 165 proximate to bottom 143. End 167 is slanted toward port 512 in chamber 164 so that air can escape chamber 164, making chamber 164 self-priming. Chamber 164 communicates with coupling 506 through horizontal port 512 and communicates with conduit 514 through vertical port 156 that is integrally molded between conduit 514 and closed end 167 of chamber 164.

Figure 13:
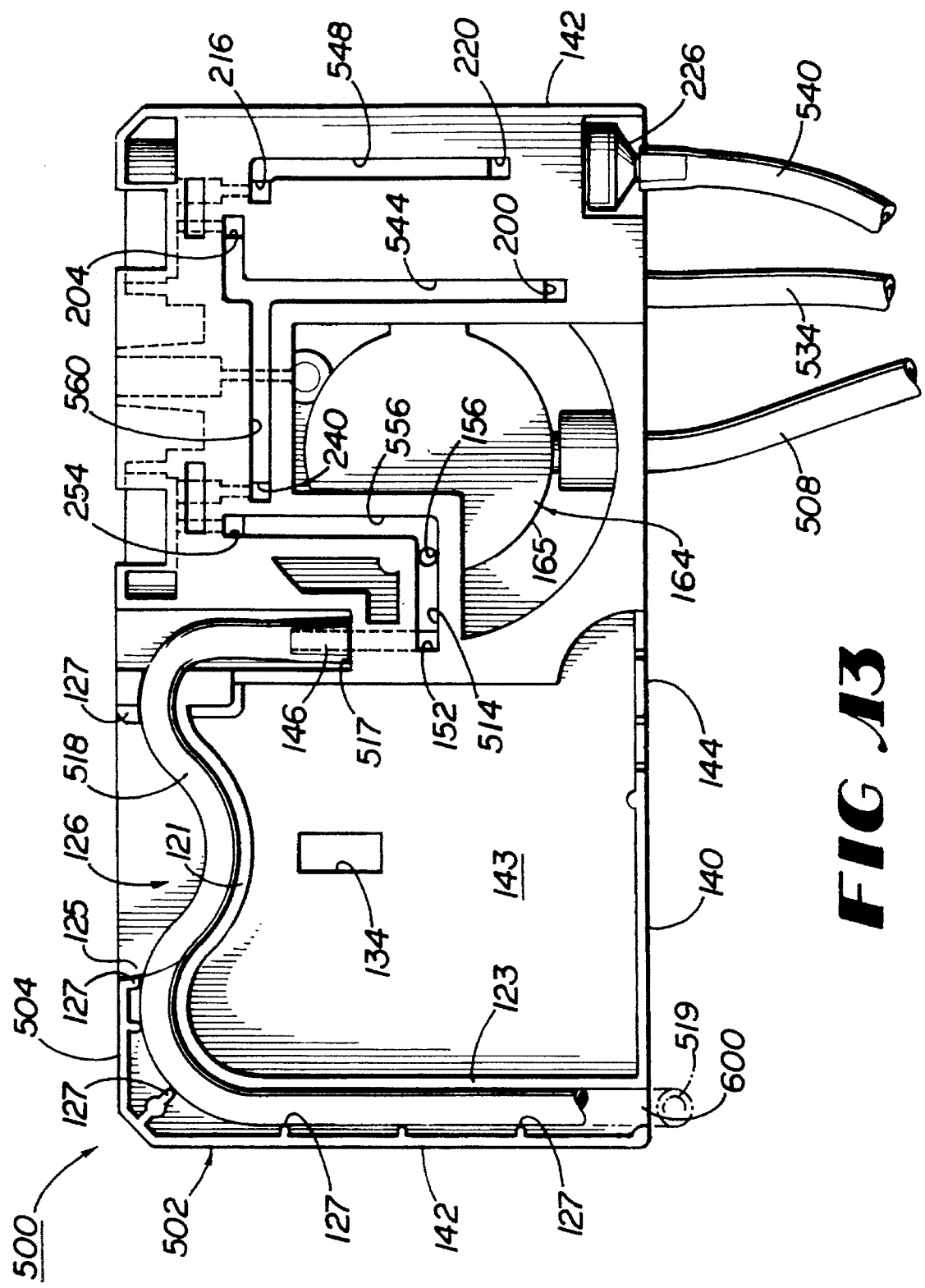
FIG. 13 is a top plan view of the cassette shown in FIG. 10 with the top gasket removed.

As can be seen in FIGS. 10, 13 and 17, interface wall 504 contains pump cutout 125, identical, circular valves 546 and 558 and recessed pressure sensing coupling 190. Valves 546 and 558 generally comprise flat, recessed valve faces 208 and 244 and diaphragm mounting rings 232 and 250, respectively, and are integrally molded in housing 502. As can be seen in FIGS. 10, 11 and 13, valve face 208 contains horizontal inlet port 210 that communicates with horizontal conduit 544 through vertical port 204 and horizontal outlet port 212 that communicates with horizontal conduit 548 through vertical port 216. Valve face 244 contains horizontal inlet port 248 that communicates with horizontal conduit 560 through vertical port 240 and horizontal outlet port 246 that communicates with horizontal conduit 514 through horizontal conduit 556 and vertical port 254. Coupling 190 is spaced between valves 546 and 558 and has an enlarged bore 191 open at one end that is substantially flush with interface wall 504 and terminating at a closed end having a horizontal pressure sensing port 186. Pressure sensing port 186 communicates with recess 173 in open end 169 of chamber 164 through vertical bore 182.

Figure 26:
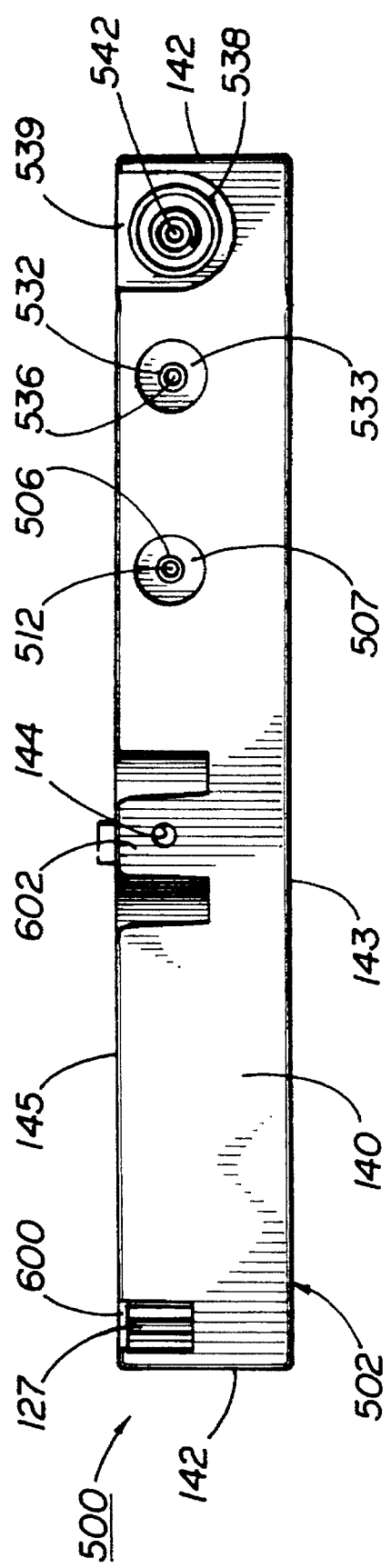
FIG. 26 is an elevational view of the wall of the cassette show in FIG. 10 opposite the interface wall shown in FIG. 17.

As can be seen in FIG. 9, 11 and 26, front wall 140 contains waste container tab 602 having an eyelet 144 to which waste container 118 may be attached, couplings 506, 532 and 538 and pump tube notch 600 from which tube 518 exits housing 502. Coupling 506 is contained within recess 507 in housing 502 and communicates with chamber 164 through horizontal port 512. Coupling 532 is contained within recess 533 in housing 502 and communicates with horizontal conduit 544 through horizontal port 536 and vertical port 200 in conduit 544. Coupling 538 is contained within enlarged recess 539 in housing 502. Coupling 538 is larger in diameter than couplings 506 and 532 and has an internal bore 529 that accepts filter element 227. Filter element 227 is retained within bore 539 by filter retainer 226 having coupling 229. Filter retainer 226 may be retained on coupling 538 by any suitable means, such as friction or suitable adhesive, and is of similar construction as housing 502. Coupling 538 communicates with horizontal conduit 548 through horizontal port 542 and vertical port 220 in conduit 548 and communicates with port 231 in coupling 229 on filter retainer 226 through filter element 227.

As can be seen in FIGS. 10, 11, 23, 24 and 25, elastic molding 262 is generally dumbbell-shaped and consists of a hollow pressure sensing port nipple 192 having a bore 195 and a sealing ring 193 equally spaced between two identical circular valve diaphragms 234 and 258 each having a sealing rim 236 and 260, respectively. Valve diaphragms 234 and 258 each have a recessed sealing face, 235 and 259, respectively, and valve actuation surface 261 and 237 opposite valve faces 235 and 259, respectively, that contain control dimples 655. Holding 262 can be made of any suitably resilient material such as silicon rubber, sanoprene or J-Von.

Figure 19:
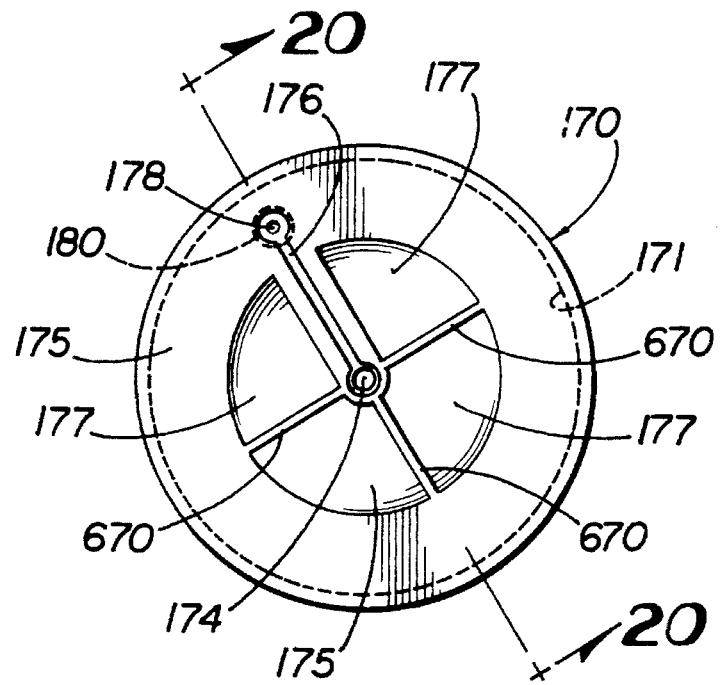
FIG. 19 is a bottom plan view of the diaphragm support of one embodiment of the present invention.
Figure 20:
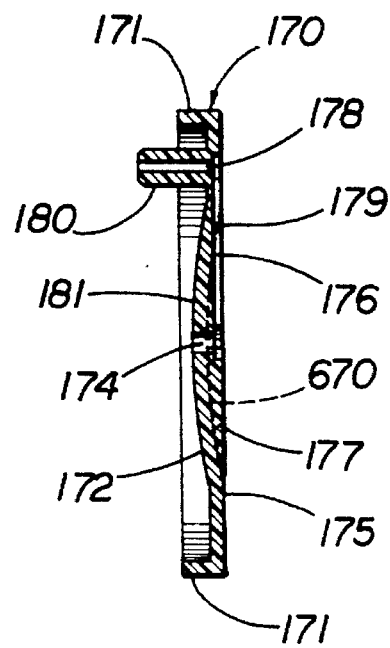
FIG. 20 is a cross section view of the diaphragm shown in FIG. 19 taken along line 20—20.
Figure 21:
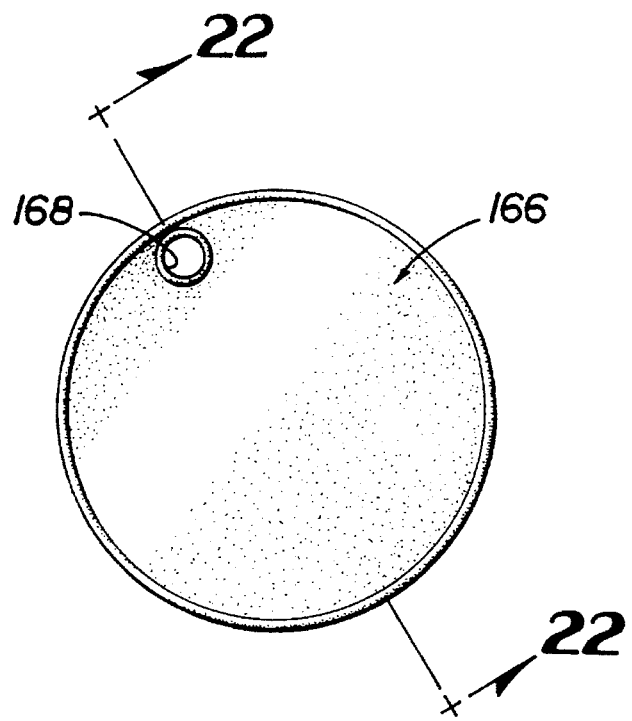
FIG. 21 is a top or bottom plan view of the pressure sensing diaphragm of the present invention.
Figure 22:
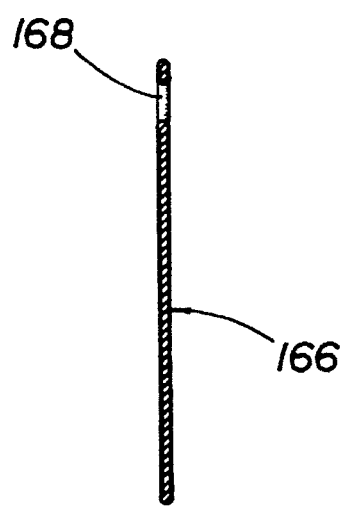
FIG. 22 is a cross sectional view of the diaphragm shown in FIG. 21 taken along line 22—22.

The pressure level within conduit 514 is monitored by a pressure sensor (not shown) within console 501. To prevent contaminated fluid from entering the pressure sensor (not shown), pressure sensing chamber 164 having cylinder 165, diaphragm 166, diaphragm cover 170 and bottom gasket 184 is used as shown in FIGS. 12, 19, 20, 21 and 22. Diaphragm 166 is slightly larger in diameter than chamber 164 and is made of an elastic material such as silicone rubber. As can be seen in FIGS. 19 and 20, diaphragm cover 170 is generally circular, has a rounded interior surface 181 having a protruding rim 171 and a coupling 180 having a port 178, an exterior surface 179 having support ribs 670 and radial channel 176, a central port 174 in fluid communication with interior surface 181 and exterior surface 179. Port 178 and port 174 communicate with each other through radial channel 176.

As can be seen in FIGS. 12 and 20, diaphragm 166 is placed on front surface 181 of diaphragm cover 170 so that hole 168 in diaphragm 166 fits over coupling 180 on cover 170. Diaphragm cover 170 containing diaphragm 168 is placed in open end 169 of chamber 164 so that rim 171 contacts recess 173 and coupling 180 journals into bore 182, which is in communication with pressure sensing port 186. Bottom gasket 184, which is round and generally the same diameter as diaphragm cover 170, is placed on exterior surface 179 of diaphragm cover 170, thereby sealing ports 174 and 178 and channel 176 into a fluid-tight conduit. Gasket 184 is similar to gasket 136, may be made of any suitable material and may attached to diaphragm cover 170 by any suitable means. However, a clear polyester film such as that sold under the trademark MYLAR® and a pressure sensitive adhesive such as heat activated polyurethene are preferred.

In use, when pump 516 is not operating and the pressure in diaphragm chamber 164 is the same as atmospheric pressure, diaphragm 166 is relaxed and lies taut against interior surface 181 of diaphragm cover 170. When pump 516 is operating, thereby reducing the pressure within conduit 514 and diaphragm chamber 164 below atmospheric pressure, diaphragm 166 is stretched toward closed end 167 of chamber 164 by the reduced pressure within diaphragm chamber 164. The stretching of diaphragm 166 creates an area of reduced pressure between diaphragm 166 and diaphragm cover 170 that is communicated to external side 179 of diaphragm cover 170 through central port 174 and to port 178 in coupling 180 through radial conduit 176. This reduced pressure is further communicated to horizontal pressure sensing port 186 through vertical bore 182 in housing 502. The pressure level in diaphragm chamber 164 is sensed by a vacuum sensor (not shown) located in console 501 and the speed of pump 516 is adjusted to keep the pressure level equal to the level set by the surgeon with panel controls 106 of console 501. The use of diaphragm chamber 164 and diaphragm 166 provides an accurate pressure signal to the pressure sensor (not shown) while keeping the sensor (not shown) free from contamination by aspirated fluid.

Cassette 500 is further assembled by placing top cover gasket 136 on top 145 of housing 502 to form closed conduits 514, 544, 548, 556, 560. Gasket 136 is similar to gasket 184 and may be made of similar materials (i.e. clear polyester film such as that sold under the trademark MYLAR® and a pressure sensitive adhesive such as heat activate polyurethene). End 517 of tube 518 is placed over coupling 146 and tube 518 is threaded through pump race 126 until discharge end 519 exits housing 502 through notch 600. As can be seen in FIG. 9, end 519 is connected to waste container 118. Elastic molding 262 is placed on interface wall 504 so that sealing face 235 lays flat against valve face 208 of valve 546 and sealing rim 236 frictionally engages ring 232 sealing off horizontal ports 210 and 212, sealing face 259 lays flat against valve face 244 of valve 558 and sealing rim 260 frictionally engages ring 250 thereby sealing off horizontal ports 246 and 248 and hollow pressure sensing nipple 192 journals within bore 191 of coupling 190 and sealing ring 193 frictionally engages coupling 190. An adhesive such as RTV silicone may be used to prevent molding 262 from being accidently dislodged from housing 502. The dual-port design of valves 546 and 558 is more reliable than conventional single port valves because faces 235 and 259 need only contact one port 210/212 or 246/248, respectively, to prevent flow through valves 546 and 558. In addition, the structure of valves 546 and 558 described above allows these valves to be used to regulate flow as well as prevent flow.

In use, interface wall 504 of cassette 500 is inserted into interface area 505 in side 503 of console 501 so that roller head 520 projects through pump cutout 125 and compresses tube 518 against depression 121 in pump race 126, two valve actuators (not shown) in interface area 505 engage dimples 655 in actuation surfaces 237 and 261, a pressure sensing probe (not shown) in interface area 505 is inserted into bore 195 of hollow pressure sensing nipple 192 and a cassette holding arm (not shown) engages cassette retaining slot 134.

Aspiration line 508, which is connected on one end to surgical handpiece 10, is connected at the other end to coupling 506. Irrigation fluid supply line 534 is connected on one end to a supply of pressurized irrigation fluid (not shown) and on the other end to coupling 532. Irrigation fluid outlet line 540 is connected on one end to surgical handpiece 10 and on the other end to coupling 229 on filter retainer 226.

Roller head 520 and tube 518 operate in the same manner as described above and draw aspiration fluid through line 508, port 512, chamber 164, conduit 514, port 146 and tube 518 where it is discharged into waste container 118. The pressure level within the closed aspiration fluid system is monitored by pressure sensing chamber 164 in cassette 500 and a pressure sensor (not shown) in interface slot 505 in console 501 in the manner described above.

Irrigation fluid is supplied to cassette 500 from a pressurized source (not shown) through irrigation supply line 534 and enters cassette 500 through irrigation fluid inlet port 536 where it is conducted to valve 546 through conduit 544. Conduit 560 branches off from conduit 544 and conducts a portion of the irrigation fluid to valve 558. In its relaxed position, sealing face 235 on diaphragm 234 seals tightly against face 208 on valve 546 to prevent the flow of irrigation fluid through vertical port 204 and out horizontal port 210. When irrigation fluid is needed, the valve actuator (not shown) in interface slot 505 of console 501 retracts so that the fluid pressure within the system pushes diaphragm 234 away from valve face 208, allowing irrigation fluid to flow up vertical port 204, out horizontal port 210 and across valve face 208 where it enters horizontal port 212, flows up vertical port 216, along horizontal conduit 548, down vertical port 220, through horizontal port 542 and filter element 227, out port 231 in coupling 229 and into handpiece supply line 540.

When the reduced pressure within aspiration fluid conduit 514 is too great, as communicated to the pressure sensor (not shown) by pressure sensing chamber 164, pump 516 may be slowed or stopped. However, when the reduced pressure within aspiration fluid conduit 514 must be quickly vented, an actuator (not shown) within interface slot 505 operates diaphragm 258 on valve 558 in a similar manner as described above to allow irrigation fluid to flow through horizontal irrigation fluid vent conduit 560, across face 244 on valve 558, into horizontal port 246 and into horizontal conduit 514 through horizontal transfer conduit 556 and vertical port 240, thereby increasing the pressure within conduit 514. The liquid or irrigation fluid vent as herein described operates more rapidly than an atmospheric vent and has a number of advantages that are described in Haines, U.S. Pat. No. 4,832,685, which is incorporated herein by reference.

The invention having now been fully described, it should be understood that it may be embodied in other specific forms or variations without departing from its spirit or essential characteristics. Accordingly, the embodiments described above are to be considered in all respects as illustrative and not restrictive.

We claim:

1. A cassette for use in combination with a surgical handpiece and a control console for controlling irrigation and aspiration fluid flows in the handpiece, comprising:

a) a housing having an external surface and an interface adapted to be held in operative association with the control console;

b) a means for generating a partial vacuum through interaction with a motive force having an inlet and a discharge line;

c) an aspiration fluid inlet coupling integrally formed in the housing;

d) an irrigation fluid inlet coupling integrally formed in the housing;

e) an irrigation fluid outlet coupling integrally formed in the housing;

f) an aspiration fluid flow passage integrally formed in the housing in fluid communication with the aspiration fluid inlet coupling and the partial vacuum generating means inlet;

g) an irrigation fluid inlet flow passage integrally formed in the housing in communication with the irrigation fluid inlet coupling;

h) an irrigation fluid outlet flow passage integrally formed in the housing in communication with the irrigation fluid inlet flow passage and the irrigation fluid outlet coupling to form a continuous irrigation fluid flow passage between the irrigation fluid inlet coupling and the irrigation fluid outlet coupling; and i) a valve spaced within the continuous irrigation fluid flow passage between the irrigation fluid inlet flow passage and the irrigation fluid outlet flow passage in operative association with a valve actuator in the console.

2. The cassette of claim 1 wherein the valve is a diaphragm valve.

3. The cassette of claim 1 wherein the partial vacuum generating means is a peristaltic pump tube and the motive force is a peristaltic pump roller head.

4. The cassette of claim 1 wherein the discharge line is in fluid communication with a waste container.

5. The cassette of claim 1 wherein the aspiration fluid flow passage and the continuous irrigation fluid flow passage comprise open channels formed in the external surface and a gasket adhered to the external surface to seal the channels fluid-tight.

6. A cassette for use in combination with a surgical handpiece and a control console for controlling irrigation and aspiration fluid flows in the handpiece, comprising:
   a) a housing having an external surface and an interface adapted to be held in operative association with the control console;
   b) a peristaltic pump tube having an inlet and a discharge line in fluid communication with a waste container;
   c) an aspiration fluid inlet coupling integrally formed in the housing;
   d) an irrigation fluid inlet coupling integrally formed in the housing;
   e) an irrigation fluid outlet coupling integrally formed in the housing;
   f) an aspiration fluid flow passage integrally formed in the housing in fluid communication with the aspiration fluid inlet coupling and the peristaltic pump tube inlet;
   g) an irrigation fluid inlet flow passage integrally formed in the housing in communication with the irrigation fluid inlet coupling;
   h) an irrigation fluid outlet flow passage integrally formed in the housing in communication with the irrigation fluid inlet flow passage and the irrigation fluid outlet coupling to form a continuous irrigation fluid flow passage between the irrigation fluid inlet coupling and the irrigation fluid outlet coupling; and
   i) a diaphragm valve spaced within the continuous irrigation fluid flow passage between the irrigation fluid inlet flow passage and the irrigation fluid outlet flow passage in operative association with a valve actuator on the console to control irrigation fluid flow in the continuous irrigation fluid flow passage.

7. The cassette of claim 6 wherein the aspiration fluid flow passage and the continuous irrigation fluid flow passage comprise open channels formed in the external surface and a gasket adhered to the external surface to seal the channels fluid-tight.

8. The cassette of claim 6 wherein the housing is plastic.

9. The cassette of claim 1 further comprising a vent for venting atmospheric air to the aspiration fluid flow passage.

10. The cassette of claim 9 wherein the vent comprises a aspiration fluid vent passage intersecting and in fluid communication with the aspiration fluid flow passage between the aspiration fluid inlet coupling and the peristaltic pump tube inlet on one end and in fluid communication with an aspiration fluid vent valve on the console on another end.

11. The cassette of claim 9 wherein the vent comprises:
   a) an aspiration fluid vent valve in the interface operated by an aspiration fluid vent valve actuator on the console;
   b) an aspiration fluid vent passage integrally formed in the housing in fluid communication with the aspiration fluid flow passage and the aspiration fluid vent valve; and
   c) an irrigation fluid transfer flow passage integrally formed in the housing in fluid communication with the irrigation fluid inlet flow passage and the aspiration fluid vent valve.

12. The cassette of claim 11 wherein the valve is a diaphragm valve.

13. The cassette of claim 11 wherein the aspiration fluid flow passage, the continuous irrigation fluid flow passage, the aspiration fluid vent passage and the irrigation fluid transfer flow passage comprise open channels formed in the external surface and a gasket adhered to the external surface to seal the channels fluid-tight.

14. A cassette for use in combination with a surgical handpiece and a control console for controlling irrigation and aspiration fluid flows in the handpiece, comprising:
   a) a housing having an external surface and an interface adapted to be held in operative association with the control console;
   b) a peristaltic pump tube having an inlet and a discharge line in fluid communication with a waste container;
   c) an aspiration fluid inlet coupling integrally formed in the housing;
   d) an irrigation fluid inlet coupling integrally formed in the housing;
   e) an irrigation fluid outlet coupling integrally formed in the housing;
   f) an aspiration fluid flow passage integrally formed in the housing in fluid communication with the aspiration fluid inlet coupling and the pump inlet;
   g) an irrigation fluid inlet flow passage integrally formed in the housing in communication with the irrigation fluid inlet coupling;
   h) an irrigation fluid outlet flow passage integrally formed in the housing in communication with the irrigation fluid inlet flow passage and the irrigation fluid outlet coupling to form a continuous irrigation fluid flow passage between the irrigation fluid inlet coupling and the irrigation fluid outlet coupling;
   i) a diaphragm valve spaced within the continuous irrigation fluid flow passage between the irrigation fluid inlet flow passage and the irrigation fluid outlet flow passage in operative association with a valve actuator on the console to control irrigation fluid flow in the irrigation fluid flow passage; and
   j) a vent comprising
      i) an aspiration fluid vent valve in the interface operated by an aspiration fluid vent valve actuator on the console,
      ii) an aspiration fluid vent passage integrally formed in the housing in fluid communication with the aspiration fluid flow passage and the aspiration fluid vent valve and
      iii) an irrigation fluid transfer flow passage integrally formed in the housing in fluid communication with the irrigation fluid inlet flow passage and the aspiration fluid vent valve.

15. The cassette of claim 14 wherein the aspiration fluid flow passage, the continuous irrigation fluid flow passage, the aspiration fluid vent passage and the irrigation fluid transfer flow passage comprise open channels formed in the external surface and a gasket adhered to the external surface to seal the channels fluid-tight.

16. The cassette of claim 14 wherein the housing is plastic.

17. A cassette for use in combination with a surgical handpiece and a control console for controlling irrigation and aspiration fluid flows in the handpiece, comprising:
   a) a housing having an external surface and an interface adapted to be held in operative association with the control console;
   b) a peristaltic pump tube having an inlet and a discharge line in fluid communication with a waste container;
   c) an aspiration fluid inlet coupling integrally formed in the housing;
   d) an irrigation fluid inlet coupling integrally formed in the housing;
   e) an irrigation fluid outlet coupling integrally formed in the housing;
   f) an irrigation fluid valve in the interface operated by an irrigation fluid valve actuator on the console;
   g) an aspiration fluid vent valve in the interface operated by an aspiration fluid vent valve actuator on the console;
   h) an aspiration fluid flow passage integrally formed in the housing in fluid communication with the aspiration fluid inlet coupling and the pump inlet;
   i) an aspiration fluid vent passage integrally formed in the housing in fluid communication with the aspiration fluid flow passage and the aspiration fluid vent valve;
   j) an irrigation fluid inlet flow passage integrally formed in the housing in communication with the irrigation fluid inlet coupling and the irrigation fluid valve;
   k) an irrigation fluid transfer flow passage integrally formed in the housing in communication with the irrigation fluid inlet flow passage and the aspiration fluid vent valve; and
   l) an irrigation fluid outlet flow,passage integrally formed in the housing in communication with the irrigation fluid valve and the irrigation fluid outlet coupling to form a continuous irrigation fluid flow passage between the irrigation fluid inlet coupling and the irrigation fluid outlet coupling.

18. The cassette of claim 17 wherein the aspiration fluid flow passage, the irrigation fluid inlet flow passage, the irrigation fluid outlet flow passage, the aspiration fluid vent passage and the irrigation fluid transfer flow passage comprise open channels formed in the external surface and a gasket adhered to the external surface to seal the channels fluid-tight.

19. The cassette of claim 17 wherein the valve is a diaphragm valve.

20. The cassette of claim 17 wherein the housing is plastic.

21. The cassette of claim 17 further comprising a means for monitoring the pressure within the aspiration fluid flow passage.

22. The cassette of claim 17 wherein the pressure monitoring means comprises:
   a) a pressure chamber having an interior and an open end integrally formed in the aspiration fluid flow passage;
   b) a resilient diaphragm having an interior side exposed to the pressure chamber interior and an exterior side;
   c) a diaphragm cover having a peripheral edge, a diaphragm side that rests against the exterior side of the diaphragm, an exterior side, a central port that communicates between the diaphragm side of the cover, a peripheral port in the peripheral edge and a radial channel on the exterior side of the cover running between and in fluid communication with the central port and the peripheral port that fits within and seals the open end of the pressure chamber;
   d) a cover gasket adhered to the exterior side of the cover to seal the radial channel;
   e) a pressure sensor port on the interface in fluid communication with the peripheral port; and
   f) a pressure sensor on the console that cooperates with the pressure sensor port.

23. A cassette for use in combination with a surgical handpiece and a control console for controlling irrigation and aspiration fluid flows in the handpiece, comprising:
   a) a housing having an external surface and an interface adapted to be held in operative association with the control console;
   b) a peristaltic pump tube having an inlet and a discharge line in fluid communication with a waste container;
   c) an aspiration fluid inlet coupling integrally formed in the housing;
   d) an irrigation fluid inlet coupling integrally formed in the housing;
   e) an irrigation fluid outlet coupling integrally formed in the housing;
   f) an irrigation fluid diaphragm valve in the interface operated by an irrigation fluid valve actuator on the console;
   g) an aspiration fluid vent diaphragm valve in the interface operated by an aspiration fluid vent valve actuator on the console;
   h) an aspiration fluid flow passage integrally formed in the housing in fluid communication with the aspiration fluid inlet coupling and the pump inlet;
   i) an aspiration fluid vent passage integrally formed in the housing in fluid communication with the aspiration fluid flow passage and the aspiration fluid vent valve;
   j) an irrigation fluid inlet flow passage integrally formed in the housing in communication with the irrigation fluid inlet coupling and the irrigation fluid valve;
   k) an irrigation fluid transfer flow passage integrally formed in the housing in communication with the irrigation fluid inlet flow passage and the aspiration fluid vent valve;
   l) an irrigation fluid outlet flow passage integrally formed in the housing in communication with the irrigation fluid valve and the irrigation fluid outlet coupling to form a continuous irrigation fluid flow passage between the irrigation fluid inlet coupling and the irrigation fluid outlet coupling; and
   m) a means for monitoring the pressure within the aspiration fluid flow passage comprising
      i) a pressure chamber having an interior and an open end integrally formed in the aspiration fluid flow passage,
      ii) a resilient diaphragm having an interior side exposed to the pressure chamber interior and an exterior side,
      iii) a diaphragm cover having a peripheral edge, a diaphragm side that rests against the exterior side of the diaphragm, an exterior side, a central port that communicates between the diaphragm side of the cover, a peripheral port in the peripheral edge and a radial channel on the exterior side of the cover running between and in fluid communication with the central port and the peripheral port that fits within and seals the open end of the pressure chamber, iv) a cover gasket adhered to the exterior side of the cover to seal the radial channel, v) a pressure sensor port on the interface in fluid communication with the peripheral port and vi) a pressure sensor on the console that cooperates with the pressure sensor port.

24. The cassette of claim 23 wherein the aspiration fluid flow passage, the irrigation fluid inlet flow passage, the irrigation fluid outlet flow passage, the aspiration fluid vent passage and the irrigation fluid transfer flow passage comprise open channels formed in the external surface and a gasket adhered to the external surface to seal the channels fluid-tight.

25. The cassette of claim 23 wherein the housing is plastic.

* * * * *